(12) United States Patent  
Wahlstrand et al.

(10) Patent No.: US 8,244,367 B2  
(45) Date of Patent: Aug. 14, 2012

(54) CLOSED LOOP LONG RANGE RECHARGING

(75) Inventors: Carl D. Wahlstrand, North Oaks, MN (US); John E. Kast, Hugo, MN (US); Timothy J. Denison, Minneapolis, MN (US); John J. Grevious, Minneapolis, MN (US); Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 610 days.

(21) Appl. No.: 12/256,811

(22) Filed: Oct. 23, 2008

(65) Prior Publication Data

US 2009/0112291 A1    Apr. 30, 2009

Related U.S. Application Data

(60) Provisional application No. 60/983,096, filed on Oct. 26, 2007.

(51) Int. Cl.  
*A61N 1/00* (2006.01)  
*A61B 5/00* (2006.01)

(52) U.S. Cl. ............... 607/60; 607/33; 607/34; 607/61; 607/62; 607/65; 128/903; 128/904

(58) Field of Classification Search .............. 607/33–34, 607/60–62, 65; 128/903–904  
See application file for complete search history.

(56) References Cited

U.S. PATENT DOCUMENTS

| 5,117,825 | A | 6/1992 | Grevious |
| 5,562,714 | A | 10/1996 | Grevious |
| 5,713,939 | A | * 2/1998 | Nedungadi et al. .............. 607/33 |
| 5,733,313 | A | 3/1998 | Barreras, Sr. et al. |
| 5,948,006 | A | 9/1999 | Mann |
| 6,047,214 | A | 4/2000 | Mueller et al. |

(Continued)

FOREIGN PATENT DOCUMENTS

WO    00/66221    11/2000

(Continued)

OTHER PUBLICATIONS

Non-published U.S. Appl. No. 13/210,569, filed Aug. 16, 2011 assigned to Medtronic entitled "Inductively Rechargeable External Energy Source, Charger, System and Method for a Transcutaneous Inductive Charger for an Implantable Medical Device".

(Continued)

*Primary Examiner* — Nicole F Lavert  
(74) *Attorney, Agent, or Firm* — Beth L. McMahon

(57) ABSTRACT

A charging system for an implantable medical device having a secondary coil. The charging system includes an external power source having at least one primary coil, a modulation, circuit operatively coupled to the primary coil and capable of driving it in a manner characterized by a charging parameter, and a sensor in communication with the modulation circuit and capable of sensing a condition indicating a need to adjust the charging parameter during a charging process. The parameter may be varied so that data sensed by the sensor meets a threshold requirement, which may be based on a patient preference, a government regulation, a recommendation promulgated by a health authority and/or a requirement associated with another device carried by the patient. In one embodiment, the regulation dictates maximum magnetic field exposure, and a field limiting circuit is employed to adjust the charging process.

35 Claims, 16 Drawing Sheets

U.S. PATENT DOCUMENTS

| | | | |
|---|---|---|---|
| 6,058,330 | A | 5/2000 | Borza |
| 6,212,430 | B1 | 4/2001 | Kung |
| 6,212,431 | B1 | 4/2001 | Hahn |
| 6,275,737 | B1 | 8/2001 | Mann |
| 6,345,203 | B1 | 2/2002 | Mueller et al. |
| 6,366,817 | B1 | 4/2002 | Kung |
| 6,400,991 | B1 | 6/2002 | Kung |
| 6,430,444 | B1 | 8/2002 | Borza |
| 6,885,353 | B2 | 4/2005 | Kurihara |
| 7,053,501 | B1 | 5/2006 | Barrass |
| 7,089,057 | B2 | 8/2006 | Heathershaw |
| 7,092,762 | B1 | 8/2006 | Loftin |
| 7,101,103 | B1 | 9/2006 | Dietz |
| 7,107,103 | B2 | 9/2006 | Schulman |
| 7,158,021 | B2 | 1/2007 | Hammett |
| 7,167,756 | B1 | 1/2007 | Torgerson |
| 7,211,986 | B1 | 5/2007 | Flowerdew |
| 7,225,032 | B2 | 5/2007 | Schmeling et al. |
| 7,239,918 | B2 | 7/2007 | Strother |
| 7,286,880 | B2 | 10/2007 | Olson |
| 7,286,881 | B2 | 10/2007 | Schommer |
| 7,428,438 | B2 | 9/2008 | Parramon et al. |
| 2004/0098068 | A1* | 5/2004 | Carbunaru et al. ............. 607/60 |
| 2004/0212344 | A1 | 10/2004 | Tamura et al. |
| 2005/0137644 | A1 | 6/2005 | Boveja et al. |
| 2006/0074465 | A1* | 4/2006 | Webb ............................. 607/60 |
| 2006/0246846 | A1 | 11/2006 | Ginggen |
| 2006/0247737 | A1 | 11/2006 | Olson |
| 2007/0078498 | A1 | 4/2007 | Rezai |
| 2007/0129767 | A1 | 6/2007 | Wahlstrand |
| 2007/0156205 | A1 | 7/2007 | Larson |
| 2007/0191907 | A1 | 8/2007 | Stein |

FOREIGN PATENT DOCUMENTS

| | | |
|---|---|---|
| WO | 03/039652 | 5/2003 |

OTHER PUBLICATIONS

International Search Report for PCT/US06/045458.

* cited by examiner

CLOSED LOOP LONG RANGE RECHARGING

RELATED APPLICATIONS

This application claims priority to provisionally-filed U.S. Patent Application No. 60/983,096 filed Oct. 26, 2007, which is incorporated herein by reference in its entirety.

This application includes some subject matter in common with U.S. Patent application Ser. No. 12/575,273 entitled "Universal Recharger for an Implantable Medical Device".

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function, which may include driving an electrical infusion pump, providing an electrical neurostimulation pulse or providing an electrical cardiac stimulation pulse. This electrical power is derived from a power source.

In some implantable medical devices electrical power can be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

While many devices and techniques have been developed to provide transcutaneous energy transfer in order to power an implantable medical device and/or charge or recharge a battery associated with an implantable medical device, external chargers associated with such devices are sometimes cumbersome and generally require the patient to take some overt step in order to associate an external charger in proximity with an internal, secondary coil associated with the implanted medical device and to initiate steps and/or procedures to accomplish a transcutaneous energy transfer in order to charge or recharge the implanted medical device. In some cases, this may require the patient to consciously remain in contact with or in the proximity of the external charging device. Such charging techniques and equipment tend to limit the flexibility and/or mobility of the patient having an implanted medical device while the device is charging.

U.S. Pat. 7,107,103 to Schulman et al, Full-Body Charger For Battery-Powered Patient Implantable Device, attempts to solve the problem of a patient having multiple implanted devices to be recharged. Schulman et al '634 discloses a full-body charger for charging one or more battery-powered devices wherein such devices are configured for implanting beneath a patient's skin for the purpose of tissue, e.g., nerve or muscle, stimulation and/or parameter monitoring and/or data communication. A support structure, typically chair-shaped or bed-shaped, is capable of supporting a patient's body while providing a magnetic field to one or more of the implanted devices using one or more coils mounted within for providing power to the implanted devices. As a result, a single, generally sequential, charging cycle can charge all of the implanted devices and thus minimize the charge time requirements for a patient and accordingly improve the patient's lifestyle.

U.S. Pat. No. 6,212,430, Kung, Electromagnetic Field Source With Detection of Position of Secondary Coil In Relation To Multiple Secondary Coils, attempts to locate a secondary coil associated with a particular implanted medical device. Kung discloses an electromagnetic field source for providing electromagnetic energy to a secondary coil, including two or more primary coils that each carry a time-varying current to produce an electromagnetic field, and a controller that selectively provides current to one or more primary coils based on their position with respect to the secondary coil. The secondary coil may be implanted in a human recipient and used to provide power for the operation of a medical device, such as an artificial heart or ventricular assist device. The primary coils may be housed in furniture. For example, they may be housed in a bed mattress or mattress pad on which the recipient rests, or in a blanket for covering the recipient. The controller includes a proximity detector that identifies those primary coils that are closest to the secondary coil and a current director that, responsive to the proximity detector, selectively drives time-varying current though the closest primary coils.

BRIEF SUMMARY OF THE INVENTION

The above-mentioned devices do not allow the patient to do normal daily activities without consciously planning the charging process. In each instance above, the patient must consciously travel to, and engage, the support structure of Schulman et al. or the furniture of Kung and initiate the charging process. This, of course, is an interruption in the daily activities of the patient and requires the patient to remember to charge the implanted medical devices at regular intervals to prevent the implanted medical device from becoming discharged.

According to one aspect of the disclosure, an external power source is passively initiated. The patient having the implanted medical device need not take any overt action to initiate the charging process. A plurality of primary coils are used, as in the Schulman et al. and Kung devices above, however, one or more of these primary coils are automatically activated by proximity to a component associated with the implanted medical device. When the primary coils are physically associated with an article into which the patient may commonly come into proximity, the automatic activation provides a passive charging system that takes no overt action on the part of the patient. This literally frees the patient to go about normal daily activities without regard to charging the implanted medical device and provides the patient with a new sense of freedom. There is minimal interaction required between the patient and the external power source, so the patient need not be burdened by such tasks as turning the external power source on, monitoring the recharge process, turning the external power source off, and so on.

Another aspect of the current disclosure relates to control over the recharge session. The recharge session may be controlled to take into account one or more government or other regulations dictating the manner in which recharge is to occur. Such regulations may govern a maximum temperature or maximum magnetic field strength to which the patient is to be exposed, for example. Such conditions are monitored and used to modulate the way the recharge is performed. For instance, if the magnetic field strength or temperature is too high based on regulations, the signal driving one or more primary coils may be modulated to change the coupling of the primary and second coils, thus bring the one or more conditions being monitored into compliance with regulations. Modulation of the signal may include modifying signal amplitude, frequency and/or duty cycle, for example.

Other information can likewise control how recharge is performed. Such information may include patient preferences and limitations governing other devices carried by a patient. For instance, a patient may carry multiple devices that are sensitive to temperature, magnetic fields and/or other conditions. Use of these other devices may be controlled by additional government regulations and/or manufacture recommendations and requirements. Recharge sessions must be conducted to take into account all of the limitations of all devices carried by the patient. In one embodiment, the current disclosure utilizes the most rigorous of all limitations covering all devices carried by the patient, as well as patient preferences, to perform recharge in comfortable, safe, and optimal manner.

According to another aspect of the system, government regulations, patient preferences, and/or limitations governing other devices carried by the patient may be automatically acquired via a communication link to a remotely-located server. This eliminates the need for a clinician to manually locate and download applicable government regulations. In some embodiments, the appropriate regulations are downloaded based on location information provided by the clinician or automatically generated by the implantable medical device.

In one scenario, the government regulation and/or limitations involve a maximum magnetic field strength. The regulation may dictate maximum magnetic field exposure to a specified anatomical structure, such as an eye or reproductive system. A field limiting circuit is employed to ensure that such requirements are met. Specifically, the field limiting circuit limits the maximum amount of flux that couples a primary coil of a recharger. In one embodiment, this is performed using a sense coil located in close proximity to the primary coil. This field limiting circuit may be used to recharge a rechargeable power source that powers the charging/recharging system.

In one embodiment, a charging system for an implantable medical device having a secondary coil is provided. The system includes a primary coil, a storage device to store information describing a regulatory requirement, and a sensor capable of sensing a condition during operation of the charging system indicating whether the regulatory requirement is being met. A modulation circuit is operatively coupled to the primary coil, the sensor, and the storage device to drive the primary coil in a manner determined by the regulatory requirement and the sensed condition when the primary coil is in proximity to the secondary coil.

Another embodiment provides a method for use with an implantable medical device that includes storing in a programmable storage device data that describes a regulatory requirement. The regulatory requirement involves controlling energizing of a secondary coil of the implantable medical device. The method also includes using a primary coil to energize the secondary coil, sensing a condition associated with energizing the secondary coil, and modifying a manner of energizing the primary coil based on whether the regulatory requirement is met as determined by the sensed condition.

Another aspect relates to a system that comprises an implantable medical device having a secondary coil, a primary coil to inductively couple to the secondary coil, a storage device to store information describing a regulatory requirement, and a circuit coupled to the primary coil and to the storage device to control a manner in which the primary coil is energized based on a determination of whether the regulatory requirement is being met.

Another example system includes a primary coil to recharge a power source of an implantable medical device (IMD) that is in proximity to at least one additional medical device. A storage device is provided to store information describing a regulatory requirement limiting a condition experienced by at least one of the additional medical devices during the recharge session. A circuit is coupled to the primary coil and to the storage device to control a manner in which the primary coil is energized based on a determination of whether the regulatory requirement is being met. This regulatory requirement may dictate a maximum magnetic field strength to which the at least one of the additional medical devices may be exposed. In one embodiment, the circuit includes a sense coil to inductively couple to the primary coil to limit the maximum magnetic field strength to which the at least one of the additional medical devices is exposed when the primary coil is recharging the power source. In another embodiment, multiple primary coils are used to recharge the power source of the IMD. In this embodiment, multiple sense coils may be provided, each to inductively couple to a respective one of the multiple primary coils. The circuit limits the maximum magnetic field strength to which the at least one of the additional medical devices is exposed by limiting a cumulative amount of magnetic flux coupling all of the multiple sense coils.

Other aspects will become apparent from the following description and the accompanying drawings.

DETAILED DESCRIPTION OF THE INVENTION

Figure 1:
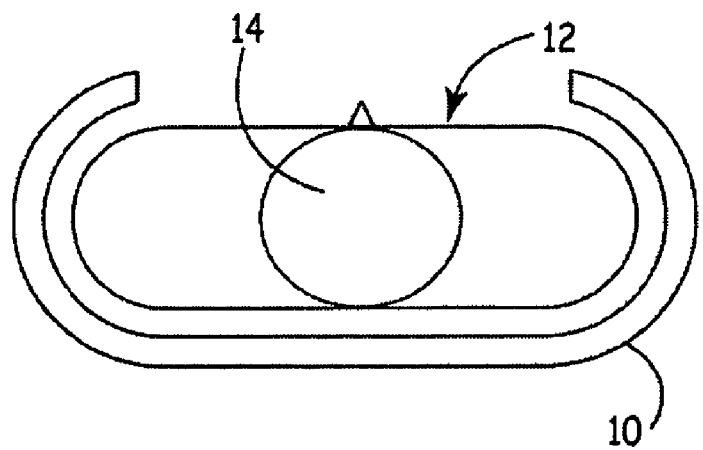
FIG. 1 illustrates a form factor for an external power source wrapping around a patient.

The entire contents of Provisional U.S. Application No. 60/742,043, the entire contents of Provisional U.S. Application No. 60/983,096 filed Oct. 26, 2007, and the entire contents of U.S. Published Patent Application No. 2007/0129767, now issued as U.S. Pat. No. 7,650,192, are hereby incorporated by reference. The entire contents of Provisional U.S. Application No. 60/982,821, entitled "Method And Apparatus For Dynamic Adjustment Of Recharge Parameters" filed Oct. 26, 2007, are incorporated by reference herein.

The passive recharging devices and methods described below allow patients to recharge their active medical devices without changing any of their daily activities. These devices may allow patients to recharge while sleeping, sitting in a chair, or walking their dog. These devices will also enable patients that would have a hard time charging a device because of its implant location to charge their devices without issues. Passive rechargers also solve the problem of frequency of patient interaction.

An external power source may be used to power or charge external or implanted medical devices placed anywhere on the body of the patient although some embodiments may be designed for specific body locations. The external power source provides form factors and other features allowing the patient to charge or recharge their medical device with no changes or minimal changes to his or her daily routines.

It is to be recognized and understood that although the focus herein is on passive charging, conventional charging or recharging systems could also benefit from the charging mechanisms described herein. Such conventional systems include those that are similar to systems discussed in the Background Section above. As one example, some of the techniques described herein could be applied to a charging system used by a patient who is traveling or otherwise unable to utilize their normal charging regimen.

In an embodiment, the external power source of the passive charging system can be semi-passive. This involves use of devices and methods that fall within the normal daily activities of the patient but that, nevertheless, the patient must actively address at some level. For example, a passive charge external power source could be built into or otherwise associated with a shirt or other garment. The patient's need to wear clothing generally falls within normal everyday activity, but does require some activity by the patient (i.e., getting dressed). Such an external charger is ambulatory and generally powered by batteries. The batteries associated with the external power source can easily be recharged conventionally by plugging into a conventional power source or plug, or by utilizing a special cradle which itself is plugged into a conventional power source. In an embodiment, the external power source is removable from the clothing, e.g., shirt, to facilitate laundry.

In general, clothes that may be used to house a passive external power source can include a vest holding an external power source for charging a medical device located in or around the area of the abdomen. A jacket may be used to charge devices located in or around the area of the abdomen or the arms. Pants may be used to charge devices located in or around the groin area or the legs. Shorts may be used to charge devices located in or around the groin area or the buttocks. An arm band may be used to charge devices located in or around the arms. A leg band may be used to charges devices located in or around the legs.

A fully passive external power source is one which the patient, caregiver or physician need only set up once. Thereafter, the patient charges their medical device simply by going about their daily routine.

An automatic turn-on feature automatically senses the proximity of the medical device to the external power source or to a primary coil associated with the external power source. Upon sensing of the external power source, energy transfer is commenced without intervention on the part of the patient. Such proximity sensing could take the form of pressure sensing, heat sensing, sensing of electromagnetic waveforms, noise detection, and/or metal sensing, as examples. Of course, other proximity sensing technologies could also be utilized.

Telemetry may be used to communicate device status to an implanted medical device, as may be accomplished to determine the status of the battery of an implanted medical device, and to determine other information such a voltage and current levels, temperature, magnetic field strength, etc. that is associated with the implanted device. In one example, telemetry could be used to terminate energy transfer when the battery of the implanted medical device has completely charged, i.e., is full. This further allows the external power source to be fully passive, without requiring patient intervention.

Various configurations of articles to physically associate either primary coils of the external power source or the external power source itself may be used.

In an embodiment, the article could be a pad that is placed on a bed for recharge while a patient is sleeping. This pad may be a thin pad that could be placed on top of bed sheets or below the sheets. This embodiment works well for a patient with a device in his back and who also sleeps on his back. Patients with devices located on their side may use this embodiment if they sleep on their sides. This bed pad embodiment does not need to be an ambulatory solution and could be plugged into the wall. This provides a large power source for the application and allows charging of the device at larger distances than ambulatory devices. This means that a patient that tosses or turns during the night could still be charging the device even while moving.

In an embodiment, the article could be a blanket allowing patients to recharge their device by simply placing the blanket over their device. This allows patients with devices in their extremities to recharge during sleep. It also allows patients with devices in their stomach area to recharge while sleeping on their backs. The blanket could also be non-ambulatory and could be powered by plugging into the wall. This power source allows larger charging distances such that the patient may move with the blanket and not worry about the loss of recharge. The passive recharge blanket may double as a heating pad by having heating conductors carried therein. If the blanket is adapted to be plugged into the wall, the power may be readily utilized to heat the conductors within the blanket as well as to charge a battery.

In an embodiment, the article could be a pad that would rest on the back of a chair. This pad could simply be placed on the back of a patient's chair so that when the patient is seated in that chair, charging is automatically initiated. The pad is especially useful for patients with devices placed in hard to reach placed in their back. The pad may be placed on the seat of the chair for charging devices placed in the buttocks or back of the leg. The pad could also be non-ambulatory allowing the power source to be from the wall. Again, this allows larger charging distances and allows the patient to move slightly during the charging session.

In an embodiment, the article could be a chair pad placed, for example, on the back of an easy chair, especially a chair routinely sat in by the patient.

In an embodiment, the article could be placed on the seat of a car routinely used by the patient.

FIG. 1 is a top view of a patient 14 surrounded by a wrap-around pad 10. In this embodiment, pad 10 is contoured around the patient's body to at least partially encompassing the abdomen 12 of patient 14. Pad 10 could take a number of shapes to fit the contours of a patient's body. For example, pad 10 could wrap around the patient's abdomen in a 180 degree manner as shown in FIG. 1. Pad 10 carries at least one primary coil for use in charging an implantable medical device.

Figure 2:
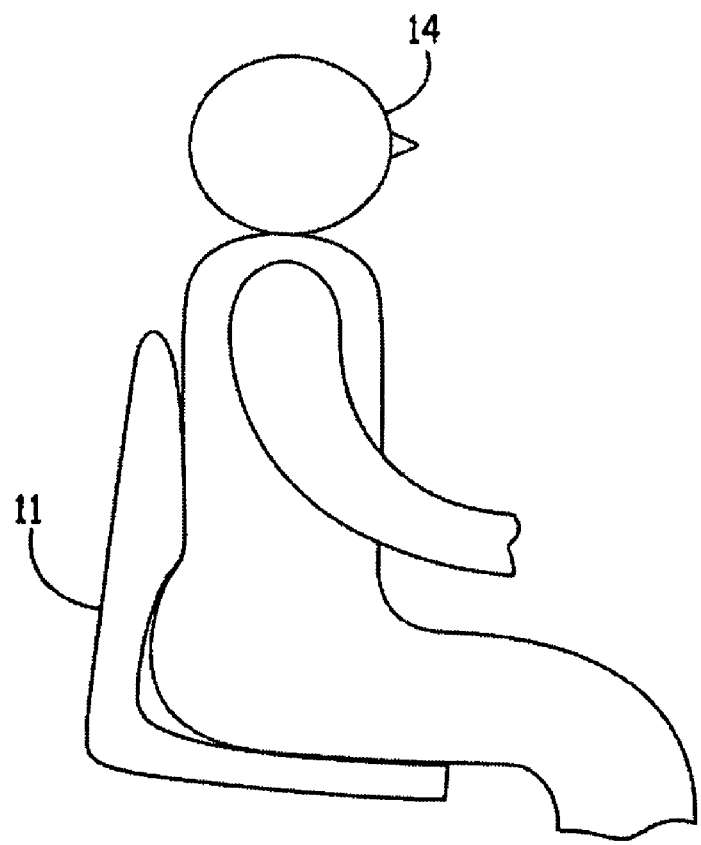
FIG. 2 illustrates a posterior shaped pad form factor for an external power source.

FIG. 2 is a side view of patient 14 sitting on pad 11 that carries at least one coil to perform passive charge or recharge. In this illustration, pad 11 is designed to fit the posterior of patient 14. In further embodiments, pad 11 could be placed in a chair that was used by patient 14 for eating purposes. This allows patient 14 to recharge during breakfast, lunch and dinner and any other meals patient 14 might have. Still further, vibration could be included in pad 11 for comfort of patient 14. Since pad 11 is generally non-ambulatory, the power source for the vibrating feature would be obtained from the wall and the vibration technology would be similar to that of commercially-available vibrating chairs.

Figure 3:
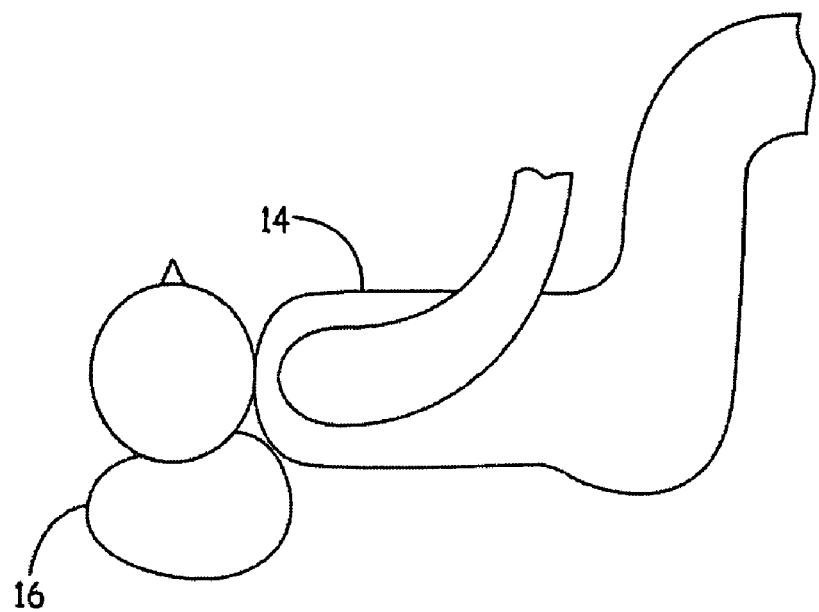
FIG. 3 illustrates a pillow form factor for an external power source.

FIG. 3 is a side view of patient 14 resting his head on a pillow 16 that includes at least one recharge coil to charge or recharge an implantable medical device. Pillow 16 allows patient 14 with a medical device placed in their head or neck to recharge passively while sleeping. Pillow 16 may be non-ambulatory and could be plugged into the wall. This allows significant charging distances and further allows the patient to move without losing recharge.

Figure 4:
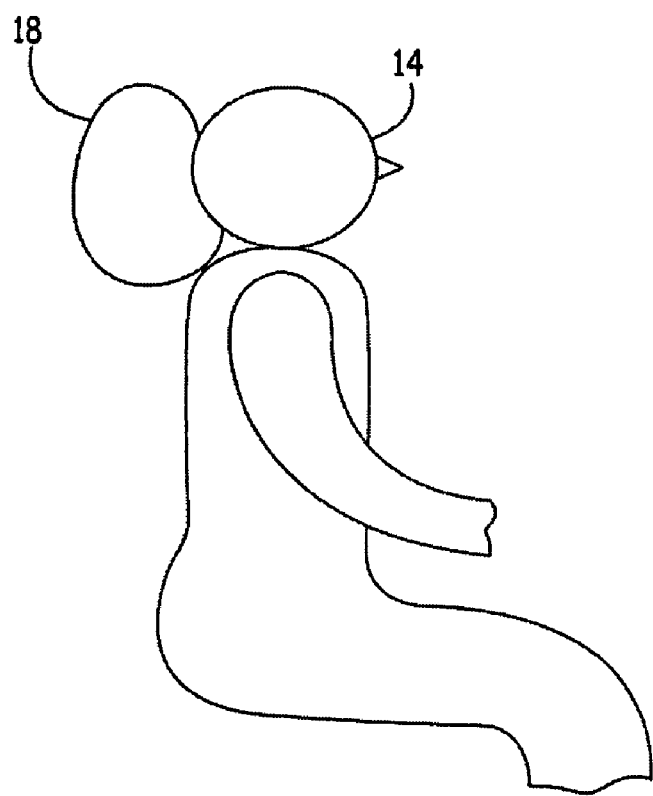
FIG. 4 illustrates a headrest form factor for an external power source.

FIG. 4 is a side view of patient 14 resting his head on a headrest 18, which could be placed on the back of a chair, on the headrest of a car seat, or any other place that patient 14 routinely rests his head. In this manner, a patient with a medical device placed in the head or neck may recharge the device passively while sitting upright or while lying down.

In an embodiment, passive charge or recharge may be accomplished in a recharge center that a patient uses during a follow-up visit to a medical clinic. This would be particularly advantageous for therapies that do not require large amounts of current such that the patient's medical device may be fully recharged when the patient goes to the medical clinic for a follow-up appointment related to the device. Such a regimen would be particularly suited for a patient that undergoes routine follow-up appointments with a medical provider. As an example, cardiac rhythm management (CRM) devices such as pacemakers and defibrillators consume low amounts of current compared to neurological devices. Moreover, CRM devices with rechargeable batteries generally have significantly longer recharge intervals than devices that deliver neurological therapies. Therefore, patients receiving CRM therapies may be able to recharge during their follow up visits to the clinic without worrying about charging between visits.

Primary coils associated with an external power source may contain a large number of small coils interconnected and packaged in a manner that allows patient 14 to use it every day. Packaging can help prevent damage to the external power source that would otherwise occur because of liquid spills, mechanical stresses, and/or other wear-and-tear to which the power source is subjected during daily use. This may result in greater longevity of the external power source. The packaging may also make the external power more comfortable for patient 14 to use on a day-to-day basis.

Packaging used with an external power source could ensure that the external power source is comfortable for patient 14 to use on a daily basis. For instance, cotton, leather, or any other comfortable fabric may be used for the purpose. In another embodiment, memory foam used for commercial pillow construction provides some consistency of location of primary coils and helps maintain a minimal distance between the primary coil(s) associated with the external power source and the secondary coil(s) associated with the medical device. Memory foam provides a soft, comfortable covering for these coils that also has some ability to mold to a patient's body.

Another fabric suited for use in this manner is polar fleece. For instance, polar fleece may be used as a blanket, a chair pad, an article of clothing, or any other article carrying one or more primary coils in proximity to a patient's body. Polar fleece provides a soft, warm, and comfortable covering for carrying the primary coil(s). Polar fleece is also relatively thin, thereby allowing the distance between the primary and secondary coils to be minimized.

In one embodiment, a garment carrying one or more primary coil(s) is constructed of a breathable fabric that wicks away moisture. By wicking away moisture from the skin, this material may be comfortably worn in direct contact with the skin for significant periods of time. An example of this material is produced by Under Armour, Inc. Other examples include GORE-TEX® fabric commercially-available from W. L Gore and Associates and COOLMAX® fabric commercially available from In vista Corporation.

Figure 5:
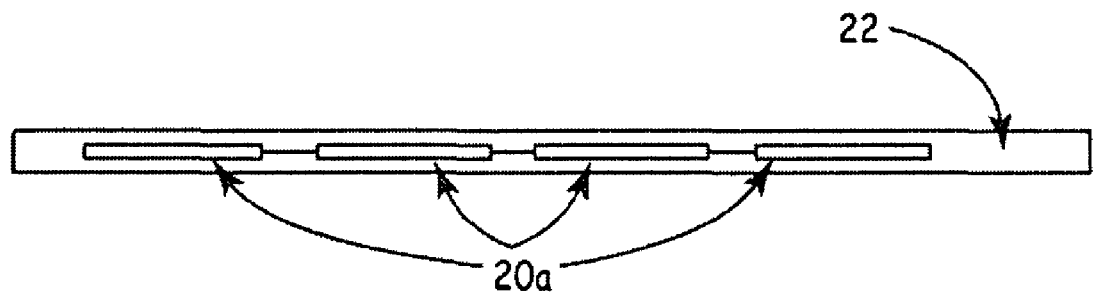
FIG. 5 illustrates a capturing of primary coils of an external power source.

FIG. 5 is a cross-sectional view of multiple primary coils 20a captured beneath a capturing material 22 to ensure that they are not damaged. This type of adaptation is especially useful for clothing form factors that will undergo stretching or bending forces and are more likely to get wet. Primary coils 20a could be over-molded with rubber. This would ensure flexibility but would hold primary coils 20a in position relative to one another. Rubber also creates a good moisture barrier to help prevent water damage to the external power source. In another embodiment, primary coils 20a may be packed in a gel. A gel could help the external power source form to the patient's body. A thin urethane covering could also be used for this purpose.

Electrical interconnect between the primary coils 20a should be able to handle significant amounts of flexing without breaking of the electrical connection. Cables of braided stranded wire could be used to interconnect primary coils 20a. Braided stranded wire can handle significant amounts of flexing and provides a number of strands (so if one wire breaks there are many other wires still making the circuit). Primary coils 20a could also consist of helically wound coils that have excellent fatigue life, and that may be of a type used in cardiac leads that are flexed during every cardiac cycle. These primary coils 20a could be covered with sonic type of polymer, such as a TEFLON® type of polymer, to keep them safe. Also flex laminate substrate such as KAPTON® or FEP TEFLON® films may be used to carry traces of the interconnect material. This flexible substrate has been shown to handle many cycles of flexing and avoids or reduces damage to the interconnect.

Primary coils 20*a* may be of all sorts of sizes and shapes. The external power source could use a high number of small coils. Each of the primary coils 20*a* may be 1 inch (2.54 cm) in diameter or less. This would allow the external power source to be highly flexible. The external power source may, in one embodiment, power only a small number of these coils that are directly over the medical device at any given time.

Figure 6:
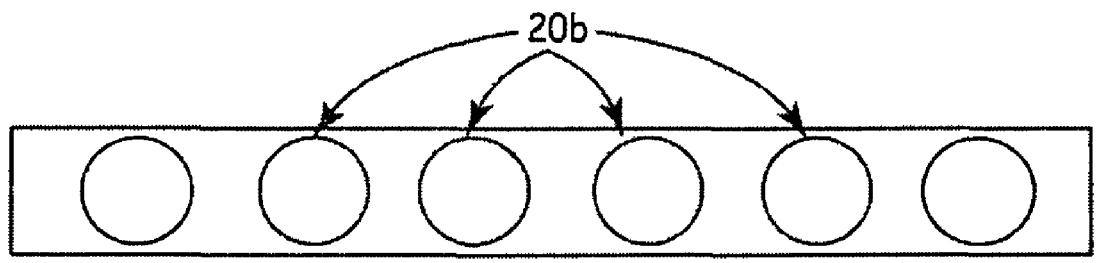
FIG. 6 illustrates a planar array of pancake primary coils.

FIG. 6 is a cross-selection view of a power source wherein primary coils 20*b* are shaped like pancakes. In this case, the array includes only one row of coils. However, multiple rows of coils could be included in another embodiment.

Figure 7:
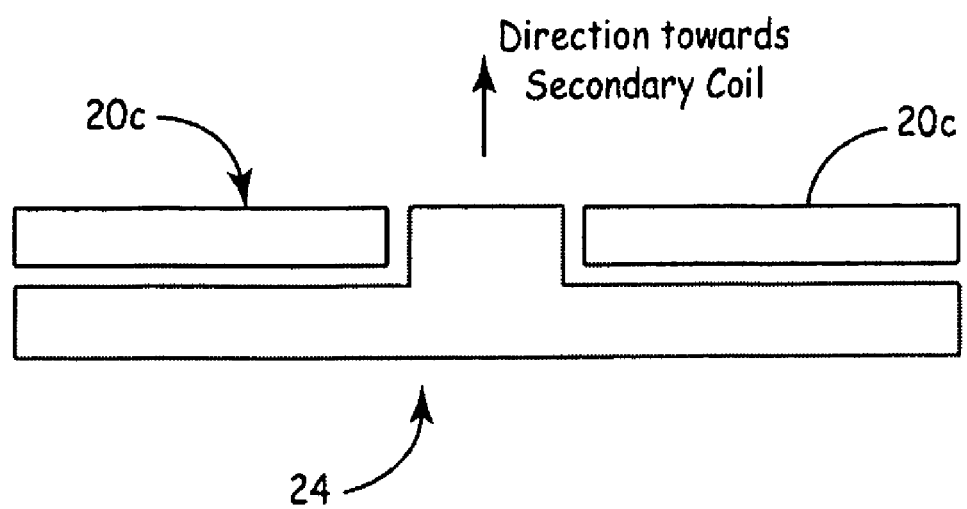
FIG. 7 illustrates use of a pot core in conjunction with a primary coil.

FIG. 7 is a cross-sectional view of an external power source according to another embodiment. In this embodiment, pot cores 24 are placed on the back side of each primary coil 20*c* to help focus the generated electromagnetic fields. Pot cores 24 could be made of materials such as manganese zinc.

Primary coils 20*c* may be constructed using wires having low impedance at high frequencies. For example, primary coils 20*c* may be constructed using Litz wire. Primary coils 20*c* could be formed by lithography or any other etching processes. Primary coils 20*c* formed by lithography could be stacked and placed in series to create coils with a higher numbers of turns than a single layer can provide. Primary coils 20 could be formed by pattern printing. Again, primary coils 20 formed by pattern printing could be stacked to create primary coils 20 with a higher numbers of turns than a single layer can provide. Primary coils 20 may be made of a highly conductive material. Copper is an example of an inexpensive, highly conductive material. Silver is another example of a highly conductive material. Other less conductive materials such as MP35n may be selected for use because such materials have a better fatigue life. Such less conductive materials may be plated with a more conductive material to reduce the resistance per unit length.

Figure 8:
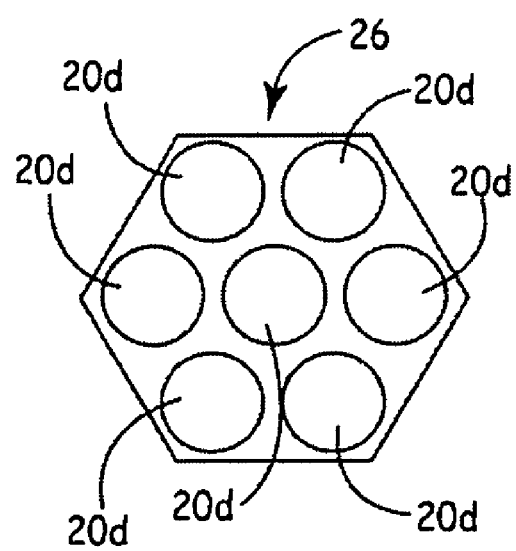
FIG. 8 illustrates a hexagonal array of primary coils.
Figure 9:
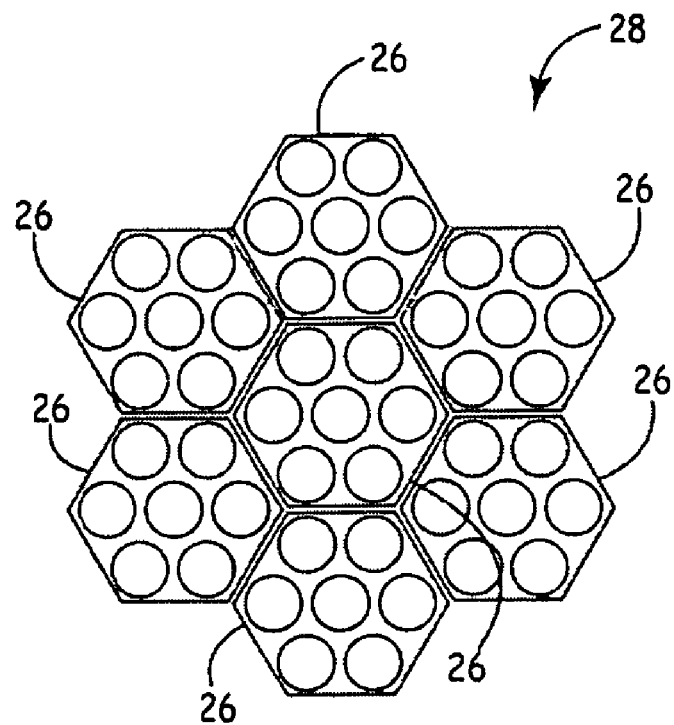
FIG. 9 illustrates a nested array of hexagonal arrays of primary coils.

FIG. 8 is a top view of an external power source with multiple primary coils 20*d* arranged in a single plane to form a hexagonal array 26. Hexagonal arrays 26 may be repeated, or nested, to form an entire passive array 28 of primary coils 20 as illustrated in FIG. 9.

Figure 10:
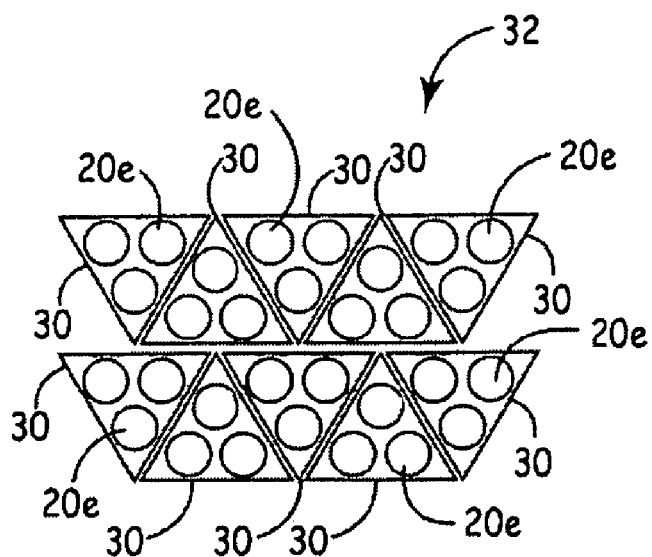
FIG. 10 illustrates a nested array of triangular arrays of primary coils.

Primary coils 20*d* may be arranged in many other types of configurations. For instance, FIG. 10 illustrates primary coils 20*e* that are positioned in a triangular configuration, with triangles 30 being repeated to form an array 32 of repeated triangles.

Figure 11A:
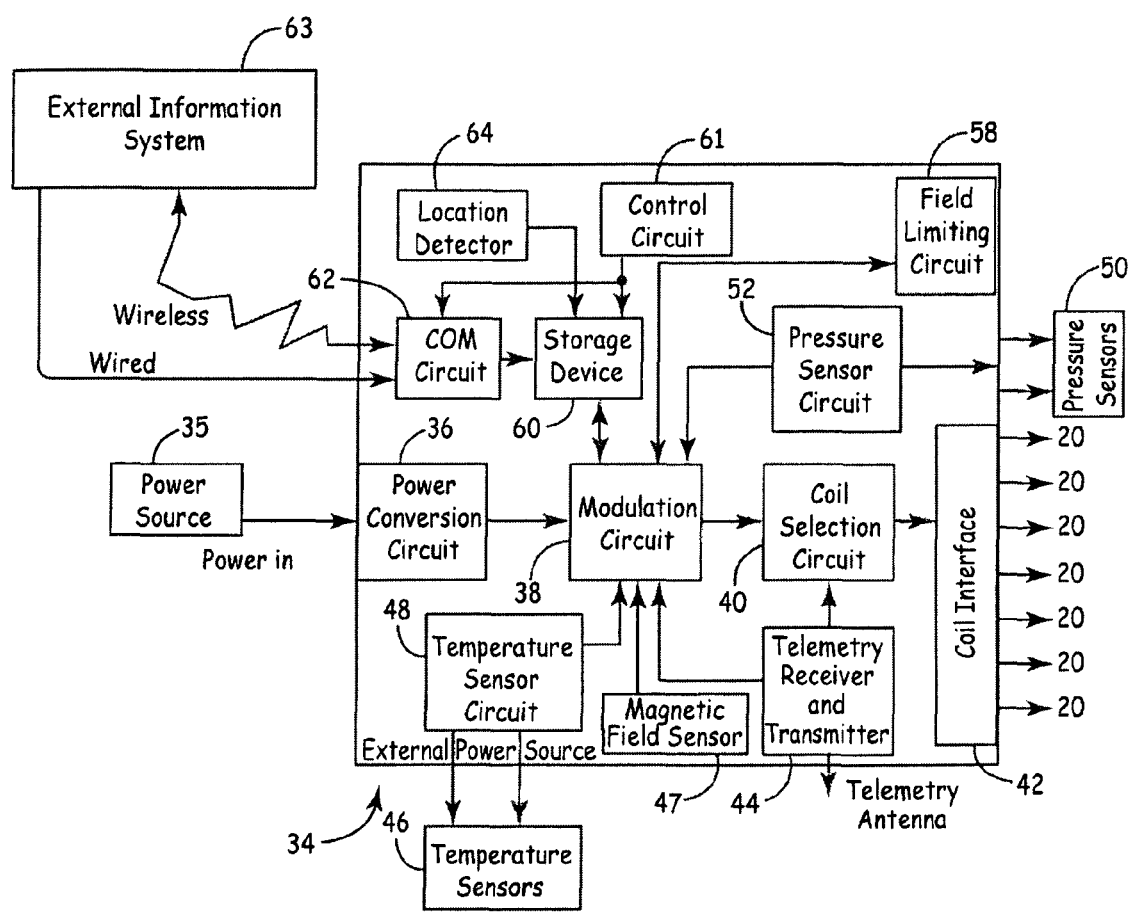
FIG. 11A is a block diagram of an external power source.

FIG. 11A is a system block diagram of electronics associated with the external power source 34. External power source 34 may receive power from power source 35, which may be a wall power source and/or may include one or more batteries. The non-ambulatory form factors such as a bed pad, a pillow, a blanket, and a chair pad allow external power source 34 to use line power. Patient 14 could simply plug external power source 34 into the wall and forget about it. Different plugs may be supplied for patients residing in various regions of the world.

The ambulatory form factors such as clothes, arm bands, etc. may require battery power for energy transfer. This could be accomplished using a power source 35 that includes Li+ rechargeable batteries. Li+ batteries can be packaged in thin, flexible foil packs. These foil packs may be placed inside the ambulatory external power source 34, and may have to be recharged. For instance, in one embodiment, recharge is initiated when patient 14 hangs these clothes on a special hanger that includes one or more primary recharge coils. In one embodiment, the batteries may be charged by field limiting circuit 58, which also limits magnetic field strength to which a patient is exposed, as will be discussed below.

Power received from power source 35 such as a wall outlet or a battery is received by power conversion circuit 36, which supplies appropriate power to modulation circuit 38. Modulation circuit 38 is a frequency generator to generate a recharge signal, typically somewhere between 8 kilohertz and 500 kilohertz. The frequency of operation may depend on the form factor of external power source 34 or the variable frequency. External power source 34 may vary the frequency during a charging session to determine the most optimal frequency for charging efficiency.

The signal generated by modulation circuit 38 is provided to coil selection circuit 40 which drives primary coils 20 through coil interface 42. Primary coils may be any of coils 20*a*-20*e* described above in relation to the various embodiments of FIGS. 5-10. Primary coils interface with one or more secondary coils of an implantable device to transmit energy through electromagnetic coupling.

External power source 34 may have a telemetry receiver and transmitter 44 enabling external power source 34 to be in communication with an implanted medical device during a charging session. Telemetry receiver and transmitter 44 may be adapted to utilize various types of telemetry protocols. A proximal telemetry system is utilized for telemetry distances of 5 centimeters or less. An arm's length telemetry system is employed for distances of up to 1 meter. This latter type of system may utilize E-field transmission (e.g., the MICS band reserved for medical device telemetry.) Arm's length telemetry may also be achieved using H-field or coupled coil transmission.

In some embodiments, it may not be possible to deliver recharge energy while communicating with the implanted medical device via a telemetry session. In such embodiments, external power source 34 may temporarily stop transmitting recharge energy in order to poll the implanted medical device for information. Recharge will remain inactivated until the telemetry session has completed. During this communication session, the implanted medical device may communicate information to the external power source that includes, for example, battery status. Such status may allow the external power source 34 to stop charging when the battery of the implanted medical device has been fully recharged.

External power source 34 may have an automatic sensor that initiates a recharge session so patient 14 is not required to take any specific action to begin a charging session. As an example, one or more temperature sensors 46 may detect whether patient 14 is in proximity to external power source 34. Such temperature sensors 46 may include thermistors, for instance, which indicate temperature changes through a corresponding change in resistance. Temperature sensor circuit 48 receives signals from temperatures sensors 46 and alerts modulation circuit 38 to commence energy transfer automatically when temperature sensors 46 provide a signal to indicate the patient is within proximity.

In another embodiment, external power source 34 may be automatically activated using a telemetry signal received from the implantable medical device. For instance, external power source 34 may continuously send out requests via telemetry. When the implanted medical device is in proximity to the external power source 34, the implanted medical device replies so that external power source 34 may initiate a recharge session.

External power source 34 may include pressure sensors 50 to commence energy transfer. When patient 14 leans against a chair pad or lies down on a bed pad, pressure sensors 50 detect the pressure and provide a signal to pressure sensor circuit 52. Pressure sensor circuit 52 alerts modulation circuit 38 to commence energy transfer.

External power source 34 may further include a magnetic field strength sensor 47 to detect magnetic field strength during recharge. Such a sensor may be a Hall effect sensor, for instance. This sensor may communicate field strength to modulation circuit 38 during recharge to control recharge parameters, as will be discussed further below.

The implanted medical device may communicate the level of the recharge current detected at the battery of the implanted medical device at a given time. This information may be communicated via a telemetry transmission, for instance. With this information, the external power source 34 may optimize energy transmission, which may include re-selecting the primary coils 20 that are being used to charge the device, and/or adjusting the amount of power that is being used to drive each of the primary coils 20.

In one embodiment, external power source 34 controls a recharge session to ensure that government requirements and other regulations that limit recharge conditions are met. For instance, standards and guidelines for permissible exposure to magnetic fields have been established by various authoritative organizations including, for example, the International Commission on Non-Ionizing Radiation protection (IC-NIRP) and the Institute of Electrical and Electronics Engineers (IEEE). These include guidelines for magnetic field exposure in several contexts, such as constant exposure in an industrial setting and intermittent exposure in a medical setting, such as exposure during an MRI procedure. Various governmental regulations set permissible limits for magnetic field exposure. These sometimes differ from jurisdiction to jurisdiction within the United States, and from country to country. It can be expected that standards, guidelines and regulations will change with time, and that new government regulations will arise as time goes on. Similar restrictions govern maximum temperatures to which the patient is exposed.

Alternatively or additionally, guidelines or standards issued by recognized authoritative entities other than government entities may be used to dictate how recharge is performed. This may be the case, for example, if guidelines and standards which are believed to be highly reliable are substantially more conservative than applicable governmental regulations.

In one embodiment, the regulations (government and/or other authoritative regulations) that control a recharge session are stored within storage device(s) 60. Storage device(s) 60 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

The government restrictions that limit recharge conditions may be stored within storage device(s) 60 by a clinician using a clinician programmer. This may be accomplished at the time the external power source 34 is configured, for instance. This will require the clinician to determine the appropriate government restrictions that will apply for the patient who will be using external power source 34. For instance, the patient may have undergone an implant procedure in a country other than the country in which the patient resides. In this case, the clinician will be required to determine what government restrictions apply in the patient's country of residence and program the external power source 34 accordingly. This may be a tedious and error-prone task.

To remove the burden of programming government restriction information into external power source 34, one embodiment of the system includes an automated mechanism for retrieving the government regulation information. According to this mechanism, a control circuit 61 is provided to initiate information retrieval. This control circuit 61 may include one or more microprocessors, FPGAs, ASICs, DSPs, microsequencers, discrete components, and/or other electronic circuit components. In an embodiment that utilizes microprocessor(s), the control circuit 61 operates according to programmed instructions that are stored within storage device(s) 60.

To automatically download information pertaining to government restrictions, control circuit 61 provides an activation signal to a communication (COM) circuit 62, prompting COM circuit to establish a communication link with an external information system 63. The communication link may be established via a hard-wired connection, as by connecting external power source 34 to a phone line, a cable connection, or any other type communication connection that may communicate via an intranet, the interne, or any other network. The communication link may instead be established via a wireless connection, as by initiating wireless communication between COM circuit 61 and a base station that is coupled to a phone line, in either event, communication is established between external power source 34 and the external information system 63, which may include one or more servers and networks maintained by the provider of external power source 34 or another medical provider. For instance, external information system 63 may be the CARELINK® system and network that is provided by Medtronic, Inc. Such system is provided to collect data for diagnosis, disease management, and care for patients that are located throughout the world. Such a system may include a database or other data repository that stores the most up-to-date government regulation data governing recharge of medical devices. This information can be automatically downloaded via the wireless or hard-wired communication link to COM circuit 62 and stored within storage device(s) 60. in this manner, a clinician does not need to be burdened by finding up-to-date regulatory information that may, or may not, be readily available.

In one embodiment, to facilitate the automatic downloading of the correct data, clinician will use a clinician programmer to program an identifier for the location in which external recharger will be primarily used. For instance, this may be a country code identifying the country of residence of the patient. This identifier may be stored within storage device(s) 60. Once so programmed, the COM circuit 62 may provide this information to external information system 63 for use in retrieving the appropriate government regulation data.

In another embodiment, external power source 34 includes a location detector 64, which may be a Global Positioning System (GPS). This location detector 64 may be used to automatically determine a current location of external power source 34 and to make this information available for use in obtaining the appropriate up-to-date government regulatory information pertaining to that location from external information system 63. For instance, upon arriving home after an implant procedure, a patient may select and active an "Update Configuration" command on a patient programmer to initiate this operation. This will automatically retrieve and store up-to-date government regulation information for the patient's current location into storage device(s) 60 for use in controlling future recharge sessions. This process may be repeated if the patient changes residence, if desired. In this manner, the patient is always assured that external power source 34 will operate according to the most up-to-date government regulations operative at the location of residence.

Location detector 64 may include an altimeter to provide altitude readings. In this manner, in one selectable mode of operation, external power source 34 may be automatically disabled when a patient is at an altitude corresponding to air travel. This is desirable since Federal Aviation Administration (FAA) regulations prohibit use of devices that will generate electromagnetic signals in the portion of the electromagnetic spectrum typically associated with recharging an implantable device. This may also be desirable so that location detector 64 is not automatically prompting the downloading of alternative regulations while a traveler is en route to a final destination.

External power source 34 further includes a field limiting circuit 58. This circuit is designed to limit a patient's magnetic field exposure based on the maximum magnetic field limitations set by government regulations, as stored within storage device(s) 60. This will be discussed further below.

Figure 11B:
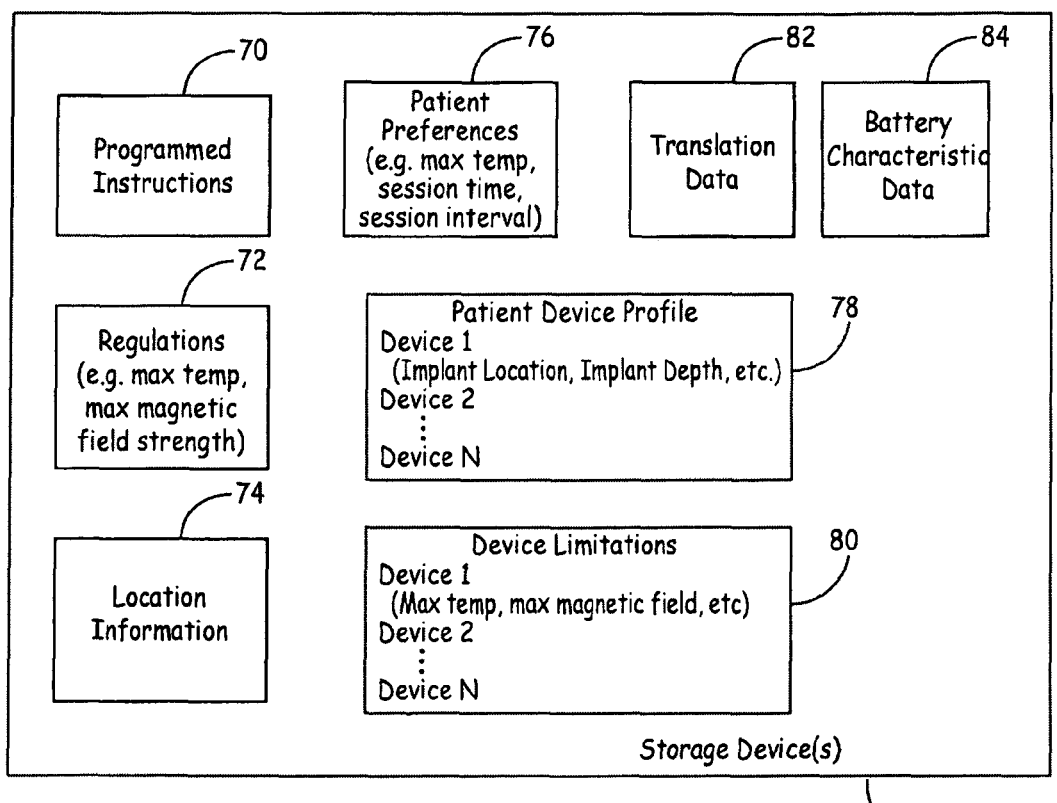
FIG. 11B is a block diagram of a storage device included within external power source.

FIG. 11B is a block diagram of storage device(s) 60 according to one embodiment. Storage device(s) store programmed instructions 70 that may be executed by control circuit 61, which may include a microprocessor such as was discussed above. Programmed instructions 70 may additionally include other instructions executed by special-purpose microprocessors, as discussed below in reference to FIG. 14.

Storage device(s) 60 may also store location information 74 indicating a primary location of use for external power source 34. As discussed above, such information may be provided by a clinician using a clinician programmer at the time external power source 34 is configured. Alternatively, such information may be automatically acquired using a location detector 64, which may be a GPS device.

Location information 74 may be made available to an external information system 63 for use in obtaining regulatory data ("regulations") 72, shown stored within storage device(s) 60. Such regulations may govern conditions that include, but are not limited to, maximum magnetic field exposure and maximum temperature limits to which a patient may be exposed during a recharge session. Regulations 72 may include any other types of government or agency regulations dictating therapy delivery via an implantable medical device.

Additional information stored within storage device(s) 60 may include patient preference data. This data may indicate, for instance, a maximum temperature to which the patient wishes to be exposed during recharge. Such preferences may be higher or lower than those set by regulations 72. During a recharge session of one embodiment, the limit that will govern how recharge occurs will be the most restrictive one of the applicable patient preference and the government regulation. For instance, if the patient preferences 76 specify a maximum skin temperature that is lower than the maximum temperature specified by the regulations 72, the patient preference data will control how recharge is performed.

Patient preferences may also indicate a preferred time between recharge sessions (i.e., recharge interval) and the maximum time spent during a single recharge session (i.e., session time). These times can be used to dictate how fast recharge will be attempted. In many systems, it is often better to perform recharge at a slower rate because it promotes longevity of the rechargeable battery within the implantable device. This can be accomplished by driving the primary coil at a lower voltage level, for instance. This type of slower recharge session can be initiated if the patient preferences 76 indicate that the patient is willing to spend more time during each recharge session and/or is willing to recharge more frequently. However, if the patient desires the fastest recharge possible and/or wants to recharge as infrequently as possible, the recharge parameters may be set to achieve the maximum energy transfer rate allowable by the other parameters, including the other patient preferences 76 such as maximum temperature and the regulations 72.

Storage device(s) 60 further may store a patient device profile 78, which includes information pertaining to all of the medical devices either implanted within, or otherwise carried on, the patient's body. Such medical devices may include cardiac devices such as pacemakers, defibrillators, synchronization devices, and the like. Other devices may include drug delivery devices to deliver medicaments such as insulin, cancer drugs, pain relieving agents, and so on. Additional devices may deliver electrical stimulation either transcutaneously, percutaneously, or via implanted leads to various areas of the patient's body, including, but not limited to, the spinal cord, the pelvic area, the head, the neck, and various ones of the patients limbs. Information in the patient device profile may identify each device, indicate location and/or depth of implant, and provide other descriptive information concerning the device, such as a make/model of the device, serial number, and so on.

A patient's device profile 78 may be entered manually by a clinician via a clinician programmer at the time external power source 34 is configured. This may be a time-consuming task, however. Preferably, this information is automatically downloaded from a database retained by external information system 63, which may be the CARELINK® system provided by Medtronic, Inc. For instance, during the configuration process, control circuit &I prompts the initiating of a communication link between external power source 34 and external information system 63 to acquire the patient's profile. This profile may be identified using unique identification information associated with the patient, such as a unique medical identification number. In FIG. 11B, this patient device profile 78 includes information describing devices 1-N. Any number of devices may be reflected by this profile. This device profile may include location information indicating where in, or on, a patient's body the device is located, as well as a depth of implant for implanted devices.

After downloading or otherwise acquiring patient device profile 78 that indicates the one or more medical devices that are implanted and/or otherwise carried by the patient, additional information pertaining to each of devices 1-N may be automatically retrieved and stored as device limitations 80. In particular, information specifying maximum conditions to which each of the devices 1-N should be exposed may be automatically downloaded and stored within storage device(s) 60. Such information may be based on government regulations, other regulatory agency information, standards information, information supplied by the providing of the device, and/or any other restrictive information dictating maximum conditions for the device.

As an example of the foregoing, some devices have physiological sensing capabilities or other functions that are sensitive to electromagnetic fields. Devices such as pacemakers and implantable cardioverter defibrillators provide therapies crucial to life support. Maintaining the proper functioning of such devices is critical. When establishing threshold conditions that are to be used to control how a recharging session is carried out, the functioning of these other devices should be considered and factored into the threshold determination. For instance, a maximum allowable magnetic field strength to which the patient is subjected during recharge may be selected based on the maximum magnetic field that can be tolerated by another medical device within the body other than the implantable medical device that is being recharged by external power source 34. Other devices may have maximum temperature restrictions, and so on. These device limitations 80 may be used along with patient preferences 76 and regulations 72 to control recharge sessions, as will be described below.

Storage device(s) 60 may also store translation data 82. This data is used to translate a limiting value for a condition that is to be regulated during recharge into some other value that, in some cases, can be more readily sensed than the original condition. For instance, it may be known that it is desirable to limit the magnetic field strength to which a device N is subjected, as described by device limitations 80. It is known that when the field strength at the implant location for device N has approximately reached this maximum value, the magnetic field strength detected by a magnetic field strength sensor (e.g. Hall effect sensor) within the implantable device that is being recharged will reach some corresponding value. This correspondence between the device limitation for device N and the other condition that can be more readily monitored (e.g., magnetic field strength at the device being recharged) can be provided by translation data. Such data may be derived empirically through sets of measurements taken when the patient is exposed to magnetic fields of varying frequencies and field strengths. Such translation data may be stored as a table or another data structure.

As another example of the foregoing, translation data 82 may translate one type of condition into another condition. For instance, it may be desirable to limit magnetic field strength at the secondary coil. Rather than directly measure and monitor magnetic field strength at this coil, translation data 82 may be provided to correlate various magnetic field strength values at the secondary coil with corresponding voltage values across the secondary coil, since voltage is proportional to field strength. Voltage across the secondary coil may then be monitored and limited to indirectly limit magnetic field strength to which a patient is exposed.

Yet another type of information stored within storage device(s) 60, which may be used when external power source 34 (FIG. 11A) is recharging a rechargeable battery includes battery characteristic data 84. Such information may be used by field limiting circuit 58 when limiting the amplitude of the magnetic field to which a patient is exposed, as will be discussed below.

Before considering how recharge sessions may be controlled using the type of information shown in FIG. 11B, a description is provided indicating how recharge is first initiated and optimized using a coil selection algorithm.

Figure 12:
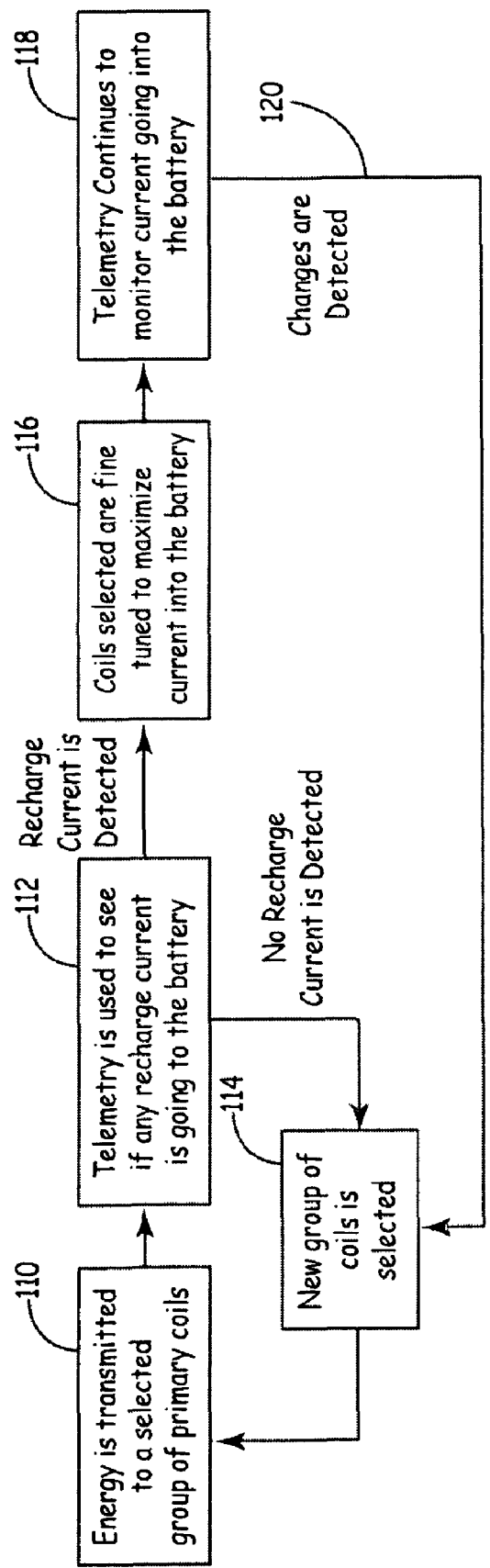
FIG. 12 is a flow chart of use of telemetry by an external power source.

A coil selection algorithm may be implemented in external power source 34 to help select which primary coils 20 should be powered at certain levels according to FIG. 12. It is feasible to have all of the primary coils 20 powered at all times, but selecting a certain subset of primary coils for higher power levels may increase the current delivered to the implanted medical device's battery and decrease the charging time.

Coil selection circuit 40 may use the resonant frequency of each of the primary coils 20. The resonant frequency of the primary coil 20 changes when the primary coil 20 is loaded by a secondary coil. External power source 34 measures the resonant frequency of all of the primary coils 20 in external power source 34 to determine which primary coils 20 are in the closest proximity to the secondary coil. External power source 34 then selects which primary coils 20 to activate and/or which of the coils to drive using the highest power.

Arm's length telemetry may also be used by coil selection circuit 40 to determine which coils to select. External power source 34 may use arm's length telemetry to determine which primary coils 20 are closest to the secondary coil. External power source 34 may energize different secondary coils 20 while communicating with the implanted medical device via arm's length telemetry to determine which primary coils 20 result in the highest recharge current within the implantable medical device. To facilitate this communication, short range telemetry may be used by coil selection circuit 40. For instance, telemetry coils and primary coils 20 may both be included in a coil array of the type shown in FIGS. 9 and 10, with the telemetry coils facilitating the short-range communication. Alternatively, primary coils 20 may be used as both recharge and telemetry coils to send and receive short-range telemetry transmissions.

FIG. 12 is a flow diagram illustrating one mechanism for optimizing a recharge session. Energy is sent (110) to a group of one or more primary coils. Telemetry is used (112) to determine whether any charge or recharge current is detected at the battery of the implanted medical device. If no recharge current is detected, a new group of primary coils 20 is selected (114) and the process returns to step 110. If recharge current is detected, primary coils 20 are fine tuned (116) to maximize current that is provided to the battery of the implanted medical device. Telemetry continues to monitor (118) current that is being provided to the battery of the implanted medical device. If changes in this current to the battery of the implanted medical device are detected (120), a new group of primary coils 20 is selected (114) and the process repeats.

External power source 34 may automatically be deactivated when an implantable device carried by patient 14 has completed charging or when patient 14 has left the proximity of external power source 34.

In one embodiment, external power source 34 determines when the implanted medical device's battery is fully charged using short-range or arm's length telemetry. In particular, a circuit within the implanted medical device determines when the battery has been fully charged. In response, a signal is transmitted automatically via telemetry to external power source 34 to indicate that the battery is fully charged, thereby prompting external power source 34 to stop transmitting recharge energy.

In another embodiment, external power source 34 utilizes temperature sensors 46 to sense when patient 14 is outside of the maximum recharge distance from the external power source 34. This may be determined by detecting a temperature decrease. If this type of temperature decrease is detected, the external power source 34 automatically stops transmitting recharge energy.

Pressure sensors 50 may also be used for this purpose. In particular, if a decrease in pressure is sensed because a patient is no longer lying or sitting on, or leaning up against, a pad, external power source 34 stops transmitting recharge energy.

In another embodiment, a patient may wear a low-power transmitter, such as one that transmits a signal at radio frequencies. Such a transmitter may be worn on a band or another article of clothing, worn as jewelry, and so on. This transmitter may be detected by the recharger when the patient is in the vicinity to prompt initiation of the recharge session.

As noted above, energy transfer may cause external power source 34 to heat up. External power source 34 preferably does not reach a temperature of more than 4° C. above the skin temperature of patient 14. Temperate sensors 46 may be used before, during, and/or after the recharge optimization process to ensure external power source 34 is not getting too warm. Temperature sensors 46 may be used to detect when patient 14 is proximal to external power source 34 and may also be used to monitor the temperature of external power source 34. It is generally accepted in the medical community that a temperature rise against the skin of patient 14 should not exceed 4° C. to ensure that there is no damage to the tissue of patient 14. Temperature sensors 46 may be placed in a particular location or throughout external power source 34 to ensure that this temperature rise is not exceeded in a particular place or at any place on external power source 34.

External power source 34 may use any type of active or passive cooling device to ensure that external power source 34 heating is kept under control. Such cooling device may utilize water cooling, fan cooling, surface area radiant cooling, refrigeration cooling, electrical cooling, thermoelectric cooling and/or any other type of cooling known in the art. In one embodiment, a wax may be employed that has a melting point around 37° C. The melting of the wax absorbs heat and retards temperature increases, acting as both a method of controlling temperature increases and a way to extract heat from the system.

Figure 13:
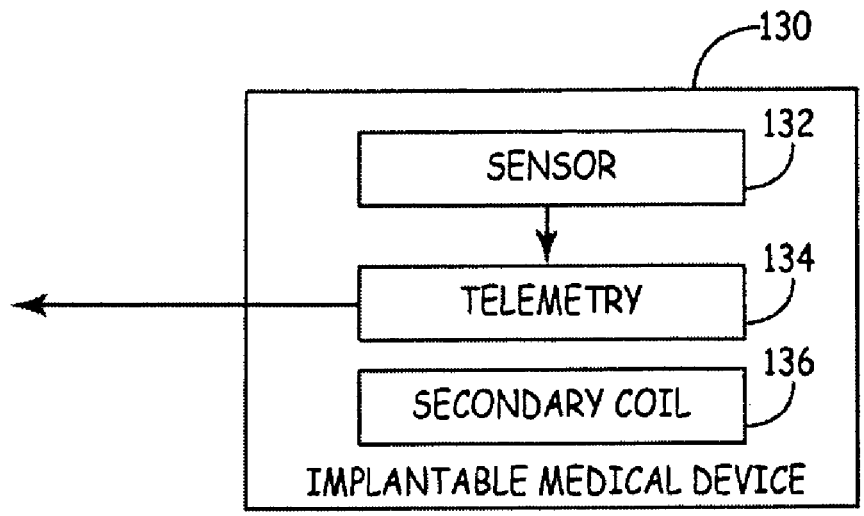
FIG. 13 is a schematic diagram showing certain elements of an implantable medical device.

FIG. 13 is a system block diagram illustrating an exemplary Implantable Medical Device (IMD) 130 that may be used in accordance with disclosed techniques. Implantable medical device 130 includes a sensor 132 (discussed below) which transmits data via a telemetry unit 134 to the external power source 34 of FIG. 11A. The implantable medical device 130 also includes a secondary coil 136 for receiving recharge energy from external power source 34.

Figure 14:
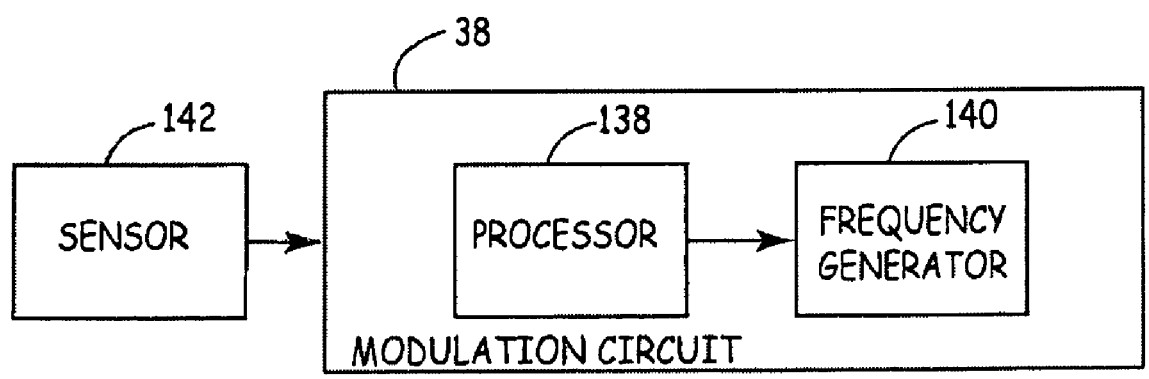
FIG. 14 is a schematic diagram of a modulation circuit.

FIG. 14 is a system block diagram illustrating modulation circuit 38 (FIG. 11A) in more detail. Modulation circuit 38 includes a processor 138 and a frequency generator 140 controlled by the processor 138. Processor 138 may be a dedicated processor that is different from any processor that is included within control circuit 61, or processor 138 may be a same processor utilized by control circuit. Modulation circuit 38 is capable of driving the primary coils 20 at a variable carrier frequency. A sensor 142, which may be, for example, a temperature sensor 46 (FIG. 11A), a pressure sensor 50, or some other type of sensor is in communication with the modulation circuit 38 to communicate sensed data to the modulation circuit 38. In this embodiment, the sensor is capable of sensing a condition that indicates a need to adjust the recharge signal parameter, which may include the frequency, amplitude and/or duty cycle of the recharge signal while an inductive charging process is taking place.

According to one embodiment, the recharge signal parameters may be adjusted so that one or more desired or predetermined conditions are met. Examples of desired or predetermined conditions include (but are not limited to): temperature thresholds at the external charger, the implantable medical device or both; thresholds or ranges for voltage and/or current amplitudes at the secondary coils; and thresholds or ranges of magnetic field strength or magnetic flux to which the patient is exposed. Any of these predetermined conditions may be dictated by regulations 72, device limitations 80 and/or patient preferences 76 (FIG. 11B). This will be discussed in further detail below.

An example of a condition that in some embodiments indicates a need to adjust a recharge signal parameter is a temperature at the external power source antenna and/or at the implantable medical device that is detected to be above a temperature threshold set by patient preferences, device limitations and/or government regulations. As illustrated in FIG. 11A, a temperature sensor may be associated with the external power source 34. In this case, temperature threshold may be an upper temperature limit chosen to indicate when the external power source 34 has heated up to a point where a reduction in temperature is desired. A reduction in temperature may be accomplished by a reduction in recharge signal frequency, signal amplitude, and/or by cycling the signal so that the signal is activated only during predetermined intervals, while being deactivated during other intervals.

In another embodiment, the temperature sensor may be located within, or associated with, the implantable medical device 130 rather than the external power source 34, as represented by sensor 132 of FIG. 13. In this case, the temperature sensor directly or indirectly measures the temperature of tissue in contact with the implantable medical device and/or the ambient body heat of the patient. Data from the sensor is communicated to the modulation circuit 38 via telemetry communication between the external power source 34 and the implantable medical device 130. An embodiment may include one or more temperature sensors in the external power source 34 and in the implantable device 130 so that temperature may be monitored in multiple places. Additionally or alternatively, multiple temperature threshold values may be programmed into the processor 138 which controls the modulation circuit 38.

Examples of temperature sensors and temperature monitoring processes which may be used in these embodiments are discussed in US Published Patent Application No. 2005/0075697 and U.S. Pat. No. 7,225,032, the entire contents of which are hereby incorporated by reference. The temperature sensor(s) may also be used as a patient proximity sensor as described above.

The threshold limits for temperature may be programmed into storage device(s) 60 and accessed by processor 138 of the modulation circuit 38. As discussed above, such limits may be chosen to comply with standards or guidelines for patient comfort. For example, as discussed above, it is a generally accepted guideline that a rise in skin temperature should not exceed 4° C. in order to assure comfort and safety for the widest range of patients. This value for threshold temperature may be programmably selected as the upper limit for temperature as sensed by a temperature sensor in the implantable device.

Another possible source for temperature threshold values is a determination of an individual patient's preference, as reflected by patient preferences 76 stored in storage device(s) 60. This can be based on a temperature range at which an individual patient is comfortable. Tolerance for heat in a charging implantable device may vary from patient to patient. A threshold which is comfortable for an individual may be determined by allowing temperature of the individual's implantable device to rise until the patient desires no further temperature increase, and then programming patient preferences 76 to reflect that temperature tolerance limit. In one alternative, a charging system may be preset with a generally accepted standard for comfortable temperature threshold, subject to adjustment to the individual's personal choice of temperature threshold if desired by the patient and/or the patient's clinician. An upper threshold appropriate to avoid injury due to heating may be preset as an upper limit, above which temperature will never be allowed to climb regardless of the patient's tolerance for heat.

Another example of a condition which may indicate a need to adjust a recharge signal parameter during the charging process is a change in distance between the secondary coil and the primary coil(s). In a system like those described herein, it is possible that a patient may move relative to the external power source 34 or to the primary coil(s) 20 in the external power source 34. Even when the patient remains in proximity to the charger, slight movements may cause the patient's implant to move relative to the primary coil(s).

One way to detect a change in distance between the secondary coil and the primary coil(s) is by monitoring voltage across, or current in, the secondary coil. These parameters are proportional to the magnetic flux within the secondary coil. The magnetic flux decreases with distance from the primary coil(s). Thus, a voltage or current sensor may be used as the sensor 132 within the implantable medical device 130 to detect a change in distance between the primary coil(s) and secondary coil. Voltage or current data is communicated from the implantable medical device to the modulation circuit 38 via telemetry. The modulation circuit 38 then adjusts parameters of the recharge signal as needed to achieve the desired voltage and/or current.

Voltage and/or current threshold values or ranges may be programmed into the system to control energy transfer. In the case of ranges, an upper limit may be selected to correspond with a maximum magnetic field exposure and a lower limit may be selected that corresponds with a minimum signal level needed for optimal power transfer. Such ranges may be programmed into processor 138 in the modulation circuit 38. Modulation circuit 38 is further adapted to increase or decrease a recharge signal parameter (e.g., frequency, amplitude, or cycling) as needed to maintain voltage or current of the secondary coil within the desired range or to meet a threshold requirement.

Figure 15:
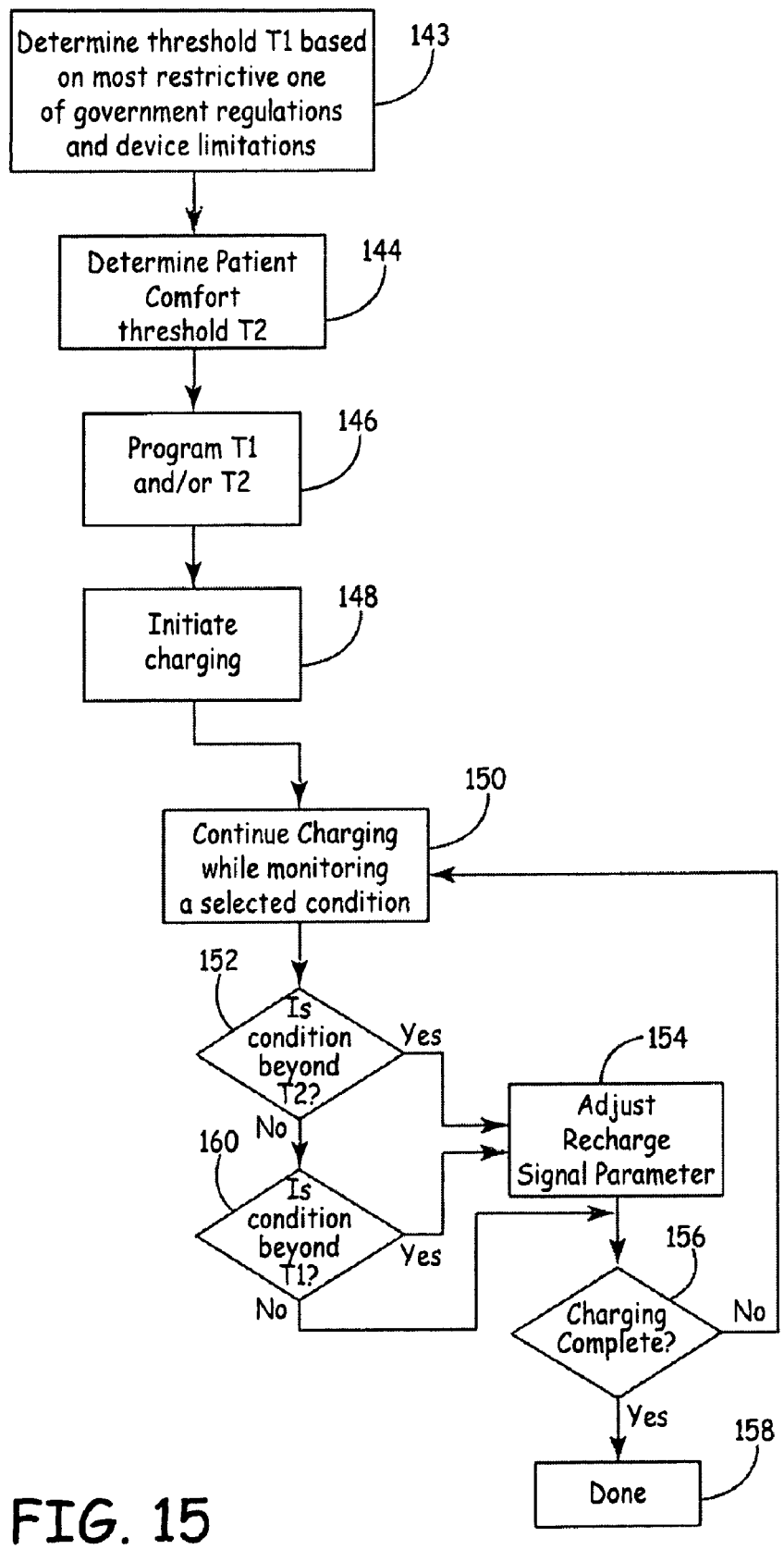
FIG. 15 is a flow chart of a temperature-based dynamic frequency adjustment process.

FIG. 15 is an example of a process for closed loop feedback using two thresholds. The thresholds may be based on temperature, magnetic field strength, or some other limiting parameter. The thresholds need not be based on the same sort of conditions. For example, a first threshold may be based on temperature and the second threshold may be based on magnetic field strength, and so on. A first threshold $T_1$ is determined (143) based on the most restrictive one of regulations 72 and the device limitations 80, as shown in FIG. 11B. For instance, threshold $T_1$ may be a lowest upper temperature limit that is selected from all upper temperature limits imposed by government regulations and device limitations. Alternatively, $T_1$ may be a lowest upper magnetic field strength limit that is selected from all such limits imposed by applicable government regulations and device limitations. $T_1$ could alternatively relate to some other monitored condition, such as a current or voltage level across secondary coil 136.

Next, a determination is made concerning a value for $T_2$, the threshold for the individual's tolerance and comfort for a condition (144). For some conditions, a second threshold value $T_2$ may not exist. For instance, in the case of maximum magnetic field strength, a patient will probably not specify a patient preference, since this field strength is not something the patient will be able to sense.

$T_1$ and/or $T_2$ may then be stored within storage device(s) 60, as may be accomplished using a programmer (146). For instance, values for $T_1$ may be programmed by a clinician, or preprogrammed as a part of the manufacturing process. In another embodiment, government regulations and device limitations are automatically downloaded from an external information system 63 based on location, patient information, and/or some other information in the manner discussed above. In some embodiments, threshold $T_1$ may be redetermined upon change of location by the patient, change of patient device profile 78, change of device limitations 80, or change of another condition affecting recharge. Such redeterminations of $T_1$ may be prompted using an "Update Configuration" command initiated on a patient programmer. This provides a means to accommodate changes to standards, regulations, location of the patient, an adjustment to the patient's device profile, and/or some other change.

Similarly, threshold $T_2$ may be programmed by the clinician or by the patient. For instance, this may be stored as patient preferences 76, and may set a maximum limit on a condition associated with recharge (e.g., a maximum temperature to which the patient wishes to be exposed). Such a limit may be higher or lower than the limit imposed by threshold $T_1$.

Next, charging is initiated (148). A sensor monitors a condition associated with recharge (e.g., temperature, magnetic field strength) while charging occurs (150). The sensed condition is communicated to a processor which compares the threshold $T_2$ (152). If the sensed condition is beyond the threshold limits (e.g., higher than a maximum threshold or lower than a minimum threshold), then the modulation circuit is controlled so as to adjust a recharge signal parameter based on the out-of-limited threshold (in this case $T_2$) while recharge continues (154). Such adjustment may involve, for example, changing a current or voltage level at the primary coil(s), changing a frequency at which charging is occurring, and/or changing the cycling of recharge so that recharge is periodically cycles on and off. It should be noted that in step 154, a different modification will likely result if the sensed condition is beyond the threshold associated with $T_2$ than when the sensed condition is beyond the threshold associated with $T_1$. For instance, if threshold $T_2$ is greater than $T_1$, a more significant adjustment will be needed than is needed if the temperature exceeds the threshold for $T_1$.

Next, it is determined whether charging is complete (156), as may be accomplished by monitoring voltage of the battery within a device. If so, the process concludes (158). Otherwise, processing returns to step 150 to continue recharge while monitoring the condition.

If the monitored condition is not beyond threshold $T_2$ in step 152, it is compared to threshold $T_1$ (160). If the condition is beyond threshold $T_1$, then a recharge parameter may be adjusted appropriately (154). If the monitored condition is within threshold $T_1$, then no adjustment is needed. It is therefore determined whether charging is completed (156). If so, the process terminates (158), otherwise, charging continues while the condition continues to be monitored (150).

Figure 16:
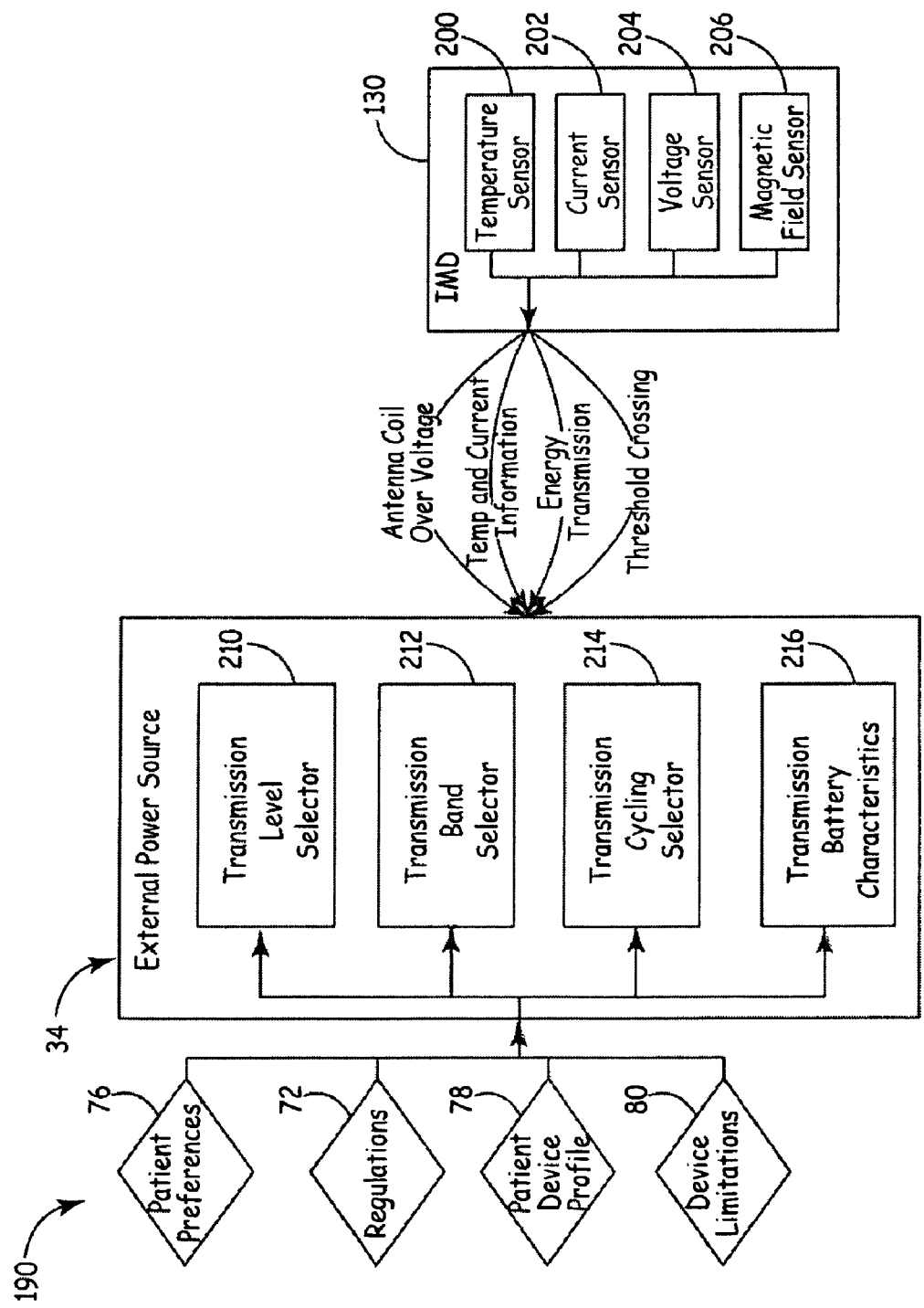
FIG. 16 is a block diagram of a closed loop energy transmissions system.

FIG. 16 is a schematic diagram illustrating one embodiment of a system for closed loop feedback suitable for a long range recharge system like that described above. In the illustrated closed loop feedback mechanism, parameters 190 may be programmed or otherwise downloaded into external power source 34. Programming may be accomplished via a clinician programmer, as discussed above, or using a user interface provided on external power source 34 itself. In the illustrated embodiment, parameters 190 include patient preferences 76, regulations 72 that include limits imposed by government regulation or other standard-setting entities, patient device profile 78, and device limitations 80.

As discussed above, device limitations 80 includes information describing thresholds associated with other devices carried on, or within, a patient's body. Although these devices may not be the target of a recharge session, they may be subjected to conditions (e.g., magnetic field conditions) imposed by the recharge session. Therefore, the limitations of these other devices should be taken into account when performing recharge.

The system may further include patient device profile information 78 such as implant depth and implant location information for each device carried on, or within, a patient's body. Implant depth and/or location information may be of particular importance when a device is in proximity to an anatomical structure which is particularly sensitive to heat or magnetic fields such as the eyes or the reproductive system, a lower threshold for heat and magnetic field strength is needed to protect these anatomical structures. For the purposes of this discussion. "in proximity to" means an implanted device is in an anatomical location which is near enough to an anatomical structure so that the heat or magnetic field has an impact on that anatomic structure. Lower thresholds may be needed when an implantable device is in proximity to sensitive anatomical structures, as prescribed by some standards and government regulations.

In the illustrated embodiment, IMD 130 includes a temperature sensor 200, a current sensor 202, a voltage sensor 204, and a magnetic field sensor 206. An IMD according to the current disclosure may include any one or more of these sensors, and/or any other sensor that detects a signal indicative of recharge efficiency and/or a condition associated with IMD 130 that is useful for controlling recharge. Data obtained from these sensors is transmitted to the external power source 34, as via a telemetry uplink communication. The external power source includes power transmission control mechanisms that can adjust one or more of transmission level (i.e., signal amplitude) 210, transmission band (i.e., frequency) 212, or power transmission cycling 214 in response to feedback from sensors which indicate that one or more conditions associated with the recharge session are beyond allowable thresholds. Such conditions may include temperature, current, and/or voltage associated with the secondary coil, and/or a magnetic characteristic of energy transfer within the IMD 130. Adjustment of energy transmission may be affected by transmission battery characteristics 216, which are the characteristics of a battery that is powering external power source in an embodiment wherein power source 35 is a battery.

As an example of the foregoing, if it is determined that magnetic field strength at the implant, as detected by magnetic field strength sensor 206, is above a threshold $T_1$ which governs a maximum magnetic field strength that should be sensed by the sensor, transmission level selector 210 may decrease the amplitude and/or frequency of the voltage that is driving one or more of primary coils 20.

In some cases, some processing steps are required to determine the threshold to be used to determine whether a measured condition of recharge is outside of allowable limits. As an example, assume that regulations indicate that a maximum allowable magnetic field strength to which a patient is to be exposed is 0.4 MicroTeslas (μT) at a frequency of 10 KHz. A translation must be performed to determine, based on implant depth, the magnetic field that will be detected by magnetic field sensor 206 when the patient is exposed to 0.4 μT. This is necessary since the signal at magnetic field sensor 206 will be attenuated by the distance between the cutaneous boundary of the patient and the secondary coil of IMD 130.

The type of translation described above could be accomplished using one or more sets of data included within translation data 82 (FIG. 11B), such as data contained in lookup tables or other data structures. This translation data, which may be determined empirically, using models, via equations, and/or some combination thereof, may take into account average, or alternatively, worst-case signal attenuation. For instance, 0.4 μT exposure at the body surface may be translated into a measured signal of 0.3 μT for an implant depth of 2 cm. Thus, the threshold $T_1$ will be set to 0.3 μT as measured by magnetic field sensor 206, rather than 0.4 μT, which corresponds to maximum field strength at the patient's body surface.

As another example, the maximum exposure at the body surface may instead be translated into a corresponding field strength as measured at the external power source 34. In yet another scenario, one of the devices other than IMD 130 described by patient device profile 78 may have a maximum magnetic field exposure limit (e.g., a limit of 0.05 μT). This device may be known to be a predetermined distance from IMD 130 and be at a predetermined implant depth, as also indicated by patient device profile 78. Translation data 82 may include a data set that may be used to determine what magnetic field value will be measured by magnetic field sensor 206 of IMD 130 when a magnetic field having a field strength of 0.05 μT exists at the other device. Again, the translation data 82 used to make the translation may be determined empirically, using equations, models and/or via some combination thereof.

In another embodiment, a maximum field strength value may instead be translated into a voltage, current, or some other signal measured in the external power source 34 or the IMD 130 (e.g., in the primary coil or secondary coil). For instance, it may be known that when the current in the secondary coil reaches 50 mA at 10 KHz, the field exposure at the body surface is approximately 0.4 μT. Therefore, when this current is measured by a current sensor associated with the secondary coil, an indication may be provided via telemetry to the external power source 34 to modulate energy transmission to reduce the magnetic field because the 0.4 μT limit at the patient's skin has been reached.

In each of the cases above, the translation from one value to another may be obtained using data developed empirically. As one example, consider a regulation dictating that the patient should not be exposed to a magnetic field having a field strength of more than 0.4 μT at the patient's body surface. A second measurement of the current, voltage, or some other signal that is associated with the secondary coil may be obtained while the maximum magnetic field is maintained at this level. This measurement may be obtained using one or more sensors of the IMD 130. If desired, this process may be performed multiple times and the various measurements processed, if desired (e.g., averaged, used to obtain a median value, etc.) The processed or unprocessed measurement(s) may be used to create a data set correlating the magnetic field value of 0.4 μT at the selected frequency to the measurement associated with the secondary coil. Different data sets may be obtained for different frequencies and different magnetic field values. The resulting translation data 82 may be stored within storage device(s) 60.

Figure 17:
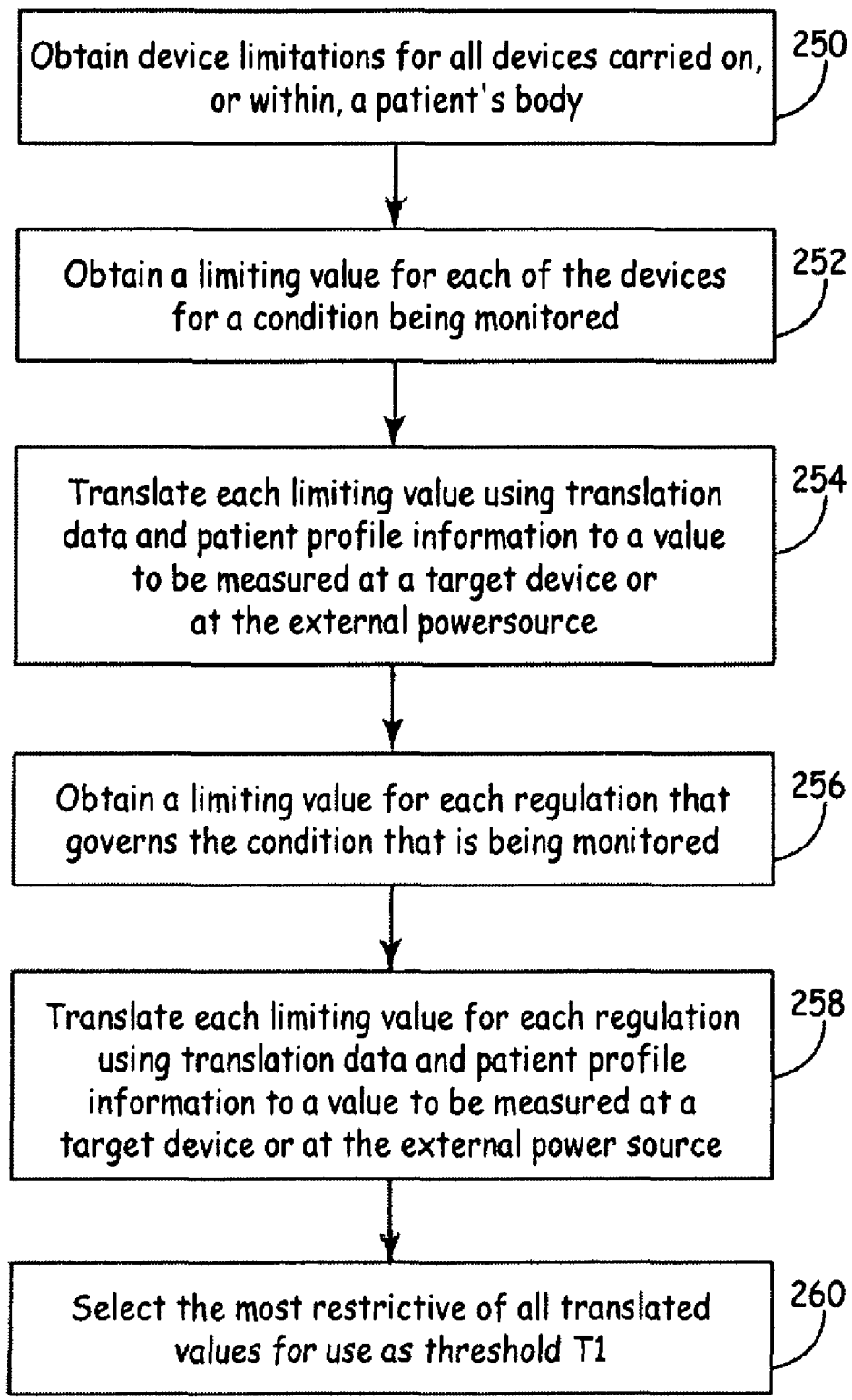
FIG. 17 is a flow diagram of one method of determining a threshold for regulation recharge sessions according to the current disclosure.

FIG. 17 is a flow diagram of one method of obtaining a threshold $T_1$ that is based on at least one of regulations and device limitations. First, device limitations are obtained that correspond to all devices carried on, or within, a patient's body (250). For a particular condition to be monitored (e.g., maximum magnetic field strength), a limiting value (e.g., maximum magnetic field strength value) is obtained for each of the devices (252). Translation data and patient profile information are used to translate each of the limiting values to a corresponding value that will be measured either by a sensor at the IMD that is the target of the recharge or a sensor in the external power source (254).

Next, a limiting value is obtained for each regulation that governs the condition that is being monitored (256). For instance, one or more regulations may exist that govern magnetic field strength, such as maximum magnetic field strength to which various organs are exposed. Translation data and patient profile information are used to translate each such limiting value to a corresponding value that will be measured by a sensor at the IMD that is the target of the recharge session or by a sensor within the external power source (258). The most restrictive of these translated values obtained in steps 254 and 258 is selected for use as threshold $T_1$ (260).

Figure 18:
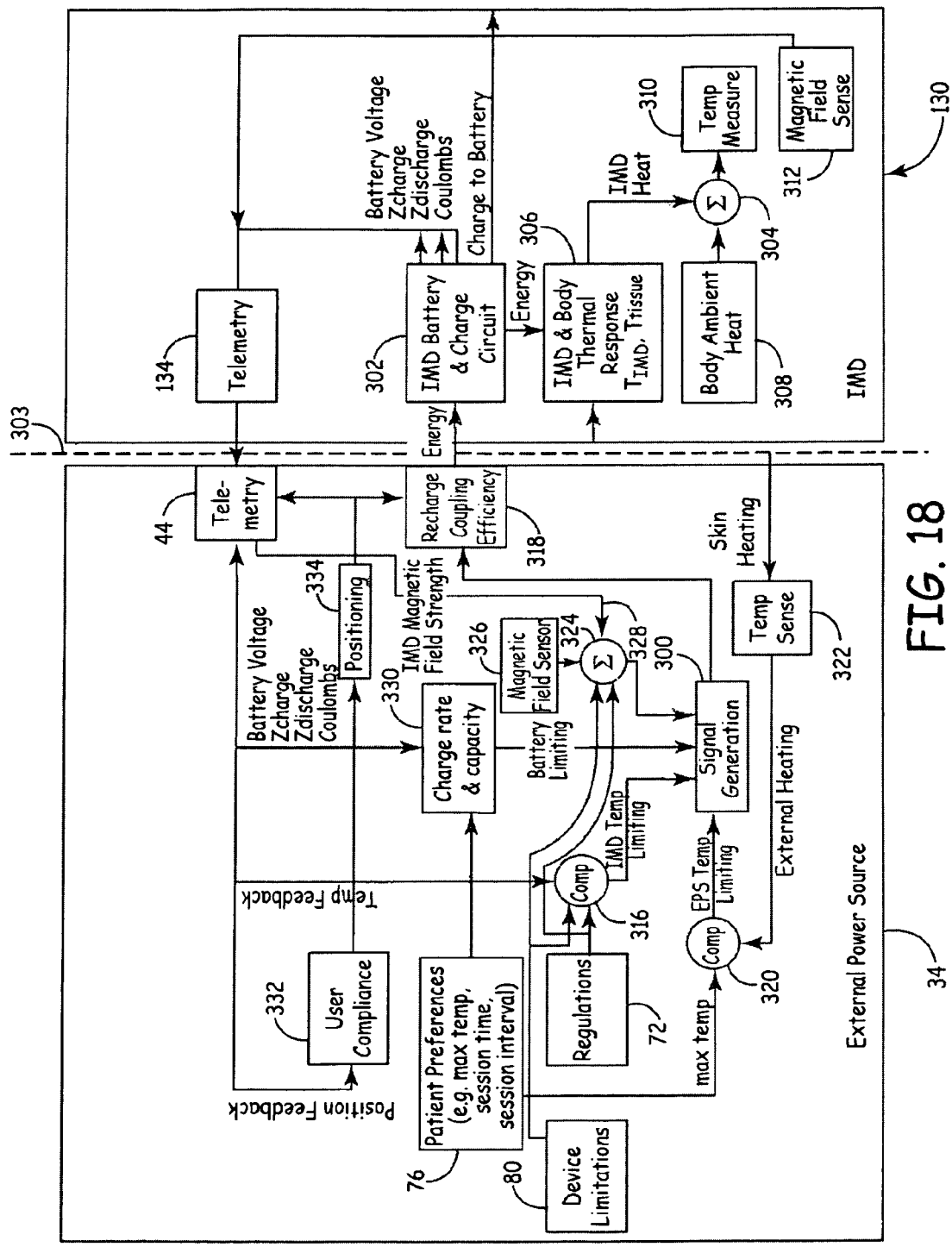
FIG. 18 is a schematic functional diagram illustrating a more detailed view of a system for closed loop feedback suitable for a long range recharge system.

FIG. 18 is a schematic functional diagram illustrating a more detailed view of a system for closed loop feedback suitable for a long range recharge system. As discussed above, an external power source 34 may store regulations 72, patient preferences 76, and device limitations 80. This information is used to perform signal generation 300, as may be accomplished by modulation circuit 38 (FIG. 11A).

Signal generation is also based on sensed conditions, such as battery voltage, the total charge provided to the battery, battery impedance when the battery is supplying power to the IMD ($Z_{discharge}$), and battery impedance when the battery is receiving power ($Z_{charge}$). Signals indicative of these sensed conditions are generated by the IMD power source (i.e., battery) and charge circuit 302 within IMD 130 and may be communicated across cutaneous boundary 303 (shown dashed) back to external power source 34. This may be accomplished via telemetry circuit 134 of the IMD 130 and telemetry circuit 44 of the external power source 34, for example.

IMD 130 includes a summing module 304 to determine the cumulative effect of body ambient heat 308, the heat of the tissue surrounding the implant $T_{Tissue}$, and the heat generated within the IMD, $T_{IMD}$. The ambient body heat 308 may change based on patient condition (e.g., may increase if the patient is feverish.) The heat of the tissue surrounding the implant, as represented by block 306, will increase during recharge as a result of the electromagnetic energy transferred during the process. Likewise, heat within the IMD, also represented by block 306, will increase during recharge. Thus, temperature increases resulting from all three of these factors are summed by summing module 304 to provide a total temperature increase that is measured by temperature measurement circuit 310. This total temperature increase is communicated back to external power source 34 via a telemetry uplink session.

Another sensor may be provided to measure magnetic field strength 312 at the IMD. This value may also be provided via telemetry uplink communication to the external power source 34.

Telemetry circuit 44 within external power source 34 provides sensed conditions received from IMD 130 for use in controlling, at least in part, how signal generation 300 is carried out. In particular, a circuit 316 compares the difference between the temperature measurement received from the IMD with the temperature stored within regulations 72 and the temperature from device limitations 80. As discussed above, in one embodiment, the temperature measurement received from the IMD represents the sum of body ambient temperature, temperature of tissue around the implant during recharge, and the temperature within the IMD during recharge. If this temperature exceeds the lesser of the temperature that is reflected by device limitations and regulations 72, compare circuit 316 generates a signal on interface 318 that influences signal generation circuit 300. In particular, if the temperature is too great within the implant as indicated by either the device limitations 80 and/or regulations 72, signal generation 300 will modify the signal driving primary coils 20 (FIG. 11A) by decreasing the amplitude, modifying cycling, and/or modifying frequency.

In a similar manner, a second compare circuit 320 receives a temperature signal related to the patient's cutaneous boundary 303 and/or a temperature within, or in relation to, external power source 34, as represented by block 322. This temperature signal is compared to the maximum temperature that is reflected by patient preferences 76. If the patient's cutaneous temperature exceeds the patient's maximum preferred skin temperature, a signal is provided to signal generation circuit 300 to limit recharge energy transferred to the IMD 130. This occurs in a manner similar to that described above with respect to compare circuit 316.

Yet another compare circuit 324 compares a measure of magnetic field strength near the external recharge antenna, as represented by block 326 and the magnetic field strength of the IMD, as provided on interface 328, with the maximum allowable magnetic field strength indicated by regulations 72 and the maximum allowable magnetic field strength indicated by device limitations. If either of these two magnetic field strength measurements exceeds the lower of the maximum magnetic field strength indicated by device limitations 80 and that indicated by regulations 72, a signal is provided to signal generation 300 to cause a reduction in the magnetic field to which the patient is exposed.

Another function performed by external power source 34 is represented by block 330 which determines a desired charge rate and capacity. This block receives the indication of IMD battery voltage, battery impedance when the battery is supplying power to the IMD ($Z_{discharge}$), and battery impedance when the battery is receiving power ($Z_{charge}$), and the total charge being provided to the battery, as is communicated by the IMD via telemetry to external power source 34. This information is used along with the patient preferences to determine capacity and rate of charge for the recharge session. For instance, if the patient is willing to tolerate a longer recharge session as indicated by patient preferences 72, it may be desirable to recharge more slowing when the battery is nearing full capacity, as indicating by battery voltage and/or $Z_{charge}$. This may promote a longer battery life, and/or may allow the battery to be "topped off" such that a longer time between recharge sessions may be possible. Thus, in this case, a signal may be issued by block 330 to signal generation logic 300 that results in a reduced charge to the IMD battery, thereby promoting slower recharge. On the other hand, if the patient is not willing to spend time recharging more slowly as indicated by patient preference data 72, the signal issued by block 330 to signal generation logic 300 may indicate that recharge is to complete as quickly as is safely possible.

In one embodiment, measurements that are indicative of recharge coupling efficiency, such as the total current being supplied to IMD battery, is provided via telemetry to a user as feedback concerning the position of the primary coil(s) 20. For instance, at the start of a recharge session before any optimization has occurred, if recharge coupling efficiency is too low, the feedback may indicate to the user that the primary coil(s) 20 are not optimally positioned with respect to IMD 130. This may be communicated to a user via a display on the external power source 34, for instance, as represented by block 332. This may prompt a user to adjust the positioning 334 of the external coil. This will result in additional feedback to the user, and so on, until the primary coil(s) are positioned to support a recharge session.

In the foregoing manner, many conditions are factored into the signal generation 300 to control recharge coupling efficiency that is established between the IMD 130 and external power source 34. Limiting factors may include, but are not limited to, ambient body temperature, increases in tissue temperature surrounding the IMD, temperature increases in the IMD itself, temperature at the patient's skin, temperature within the external power source 34, magnetic field strength in the IMD and/or in the proximity of the external power source, and battery conditions of the rechargeable battery. Limits may be imposed by one or more of patient preferences 72, device limitations 80 and regulations 72.

The foregoing describes making adjustments to a charging parameter (e.g., current, voltage, frequency, cycling, etc.) to modify signal generation 300 and to thereby control recharge based on a sensed parameter value (e.g., temperature, magnetic field strength, a voltage, a current, etc.). As discussed above, signal generation 300 may be performed by modulation circuit 38 of FIGS. 11A and 14. Another approach to controlling the recharge of an IMD battery adjusts field limiting circuit 58 of FIG. 11A. This is described in reference to FIGS. 19-21 below.

Figure 19:
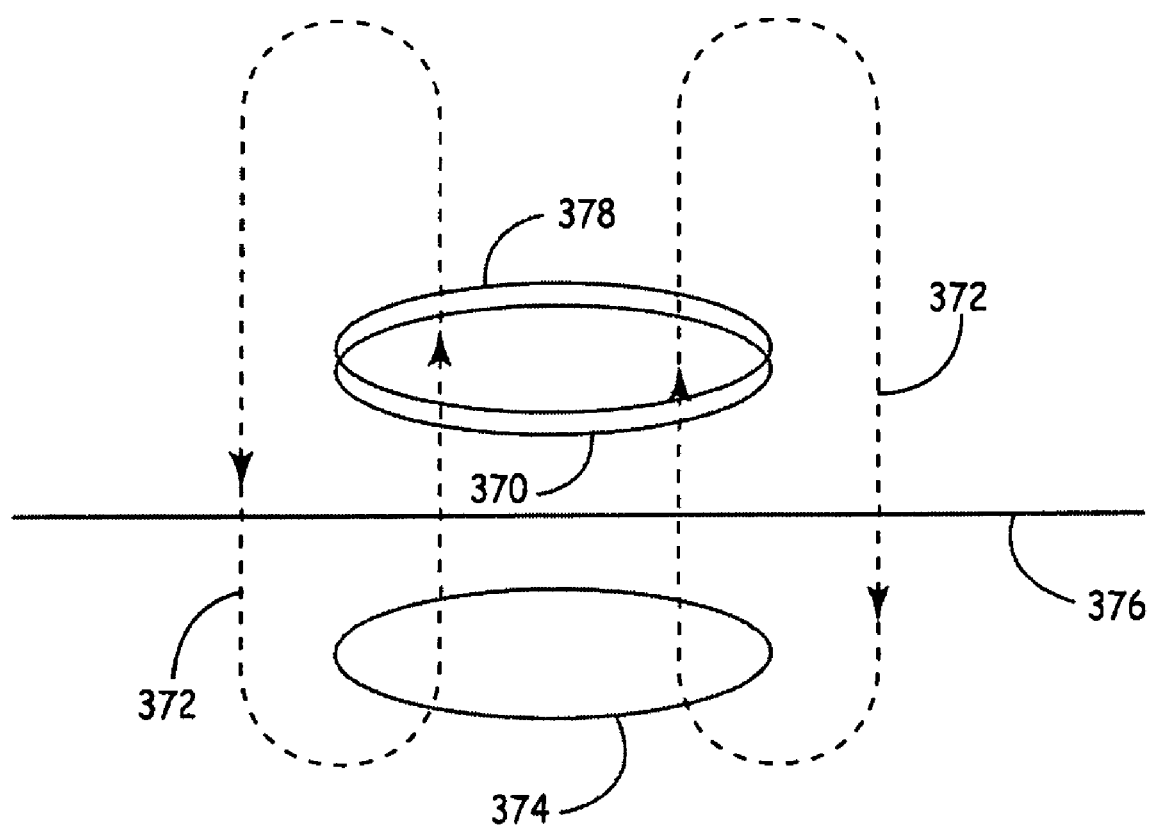
FIG. 19 is a flux diagram including a primary coil, a secondary coil, and a sense coil.

FIG. 19 is a flux diagram including a primary coil 370 of a recharging device, which may be similar to any of coils 20 (FIG. 11A). FIG. 19 further illustrates secondary coil 374 of an IMD, which may be similar to secondary coil 136 of IMD 130 (FIG. 13). As is known in the art, an alternating current having a frequency f that is generated in a primary coil 370 induces a magnetic field represented by flux lines 372. The magnetic field, in turn, results in an alternating current in a secondary coil 374 implanted below cutaneous boundary 376 of a living being.

An alternating voltage is generated across both the primary coil 370 and secondary coil 374 while the primary coil is being driven at the frequency f. For a coil having N turns and an area A, a voltage across the coil is related to the maximum strength of the magnetic field that is coupling the coil, $B_{max}$, according to the following equation:

$$V_{coil} = NA 2\pi f B_{max}$$

Thus, the maximum field strength of the magnetic field at a given coil can be regulated by controlling the voltage across the coil, as follows:

$$B_{max} = V_{coil}/(NA 2\pi)$$

In view of the foregoing, one way to limit maximum magnetic field strength, $B_{max}$, at a coil is to "clamp" the voltage across the coil to a certain maximum voltage. According to one embodiment, field limiting circuit 58 (FIG. 11A) may be used for this purpose. Field limiting circuit provides a sense coil 378 that may be approximately the same size and shape as the primary coil and that may be positioned in close proximity to primary coil 372. In this configuration, the maximum magnetic field strength $B_{max\_primary}$ at the primary coil substantially equals the maximum magnetic field strength $B_{max\_sense}$ at the sense coil. That is, approximately the same amount of flux 372 couples both the primary and sense coils.

The field limiting circuit is utilized to clamp the voltage of the sense coil, $V_{sense}$, to some selected voltage that is programmable. This regulates $B_{max\_sense}$ to a programmable value determined by the equation $$B_{max\_sense} = V_{sense}/(N_{sense} A_{sense} 2\pi f)$$

This, in turn, regulates the magnetic field strength at the primary coil.

$B_{max\_sense}$ at sense coil 378 can be limited via field limiting circuit 58 to a value that corresponds to the maximum magnetic field strength value measured at some predetermined location on the patient's body (e.g., patient's skin) to which the patient is subjected. This thereby limits the patient's exposure to the magnetic field in a selectable manner that may be determined by regulations 72, device limitations 80, and/or patient device profile 78.

Figure 20:
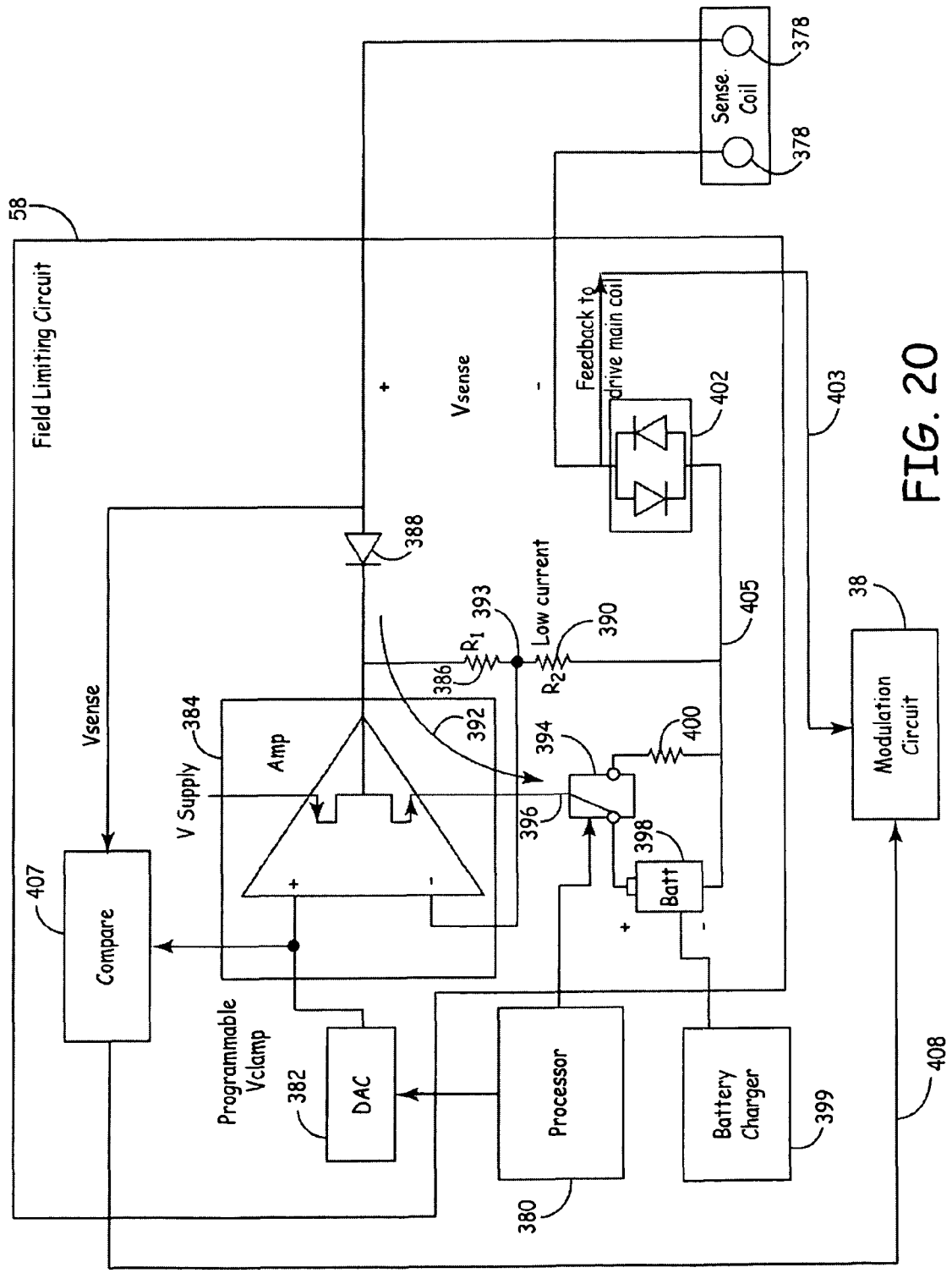
FIG. 20 is a system block diagram of one embodiment of a field-limiting circuit.
Figure 21:
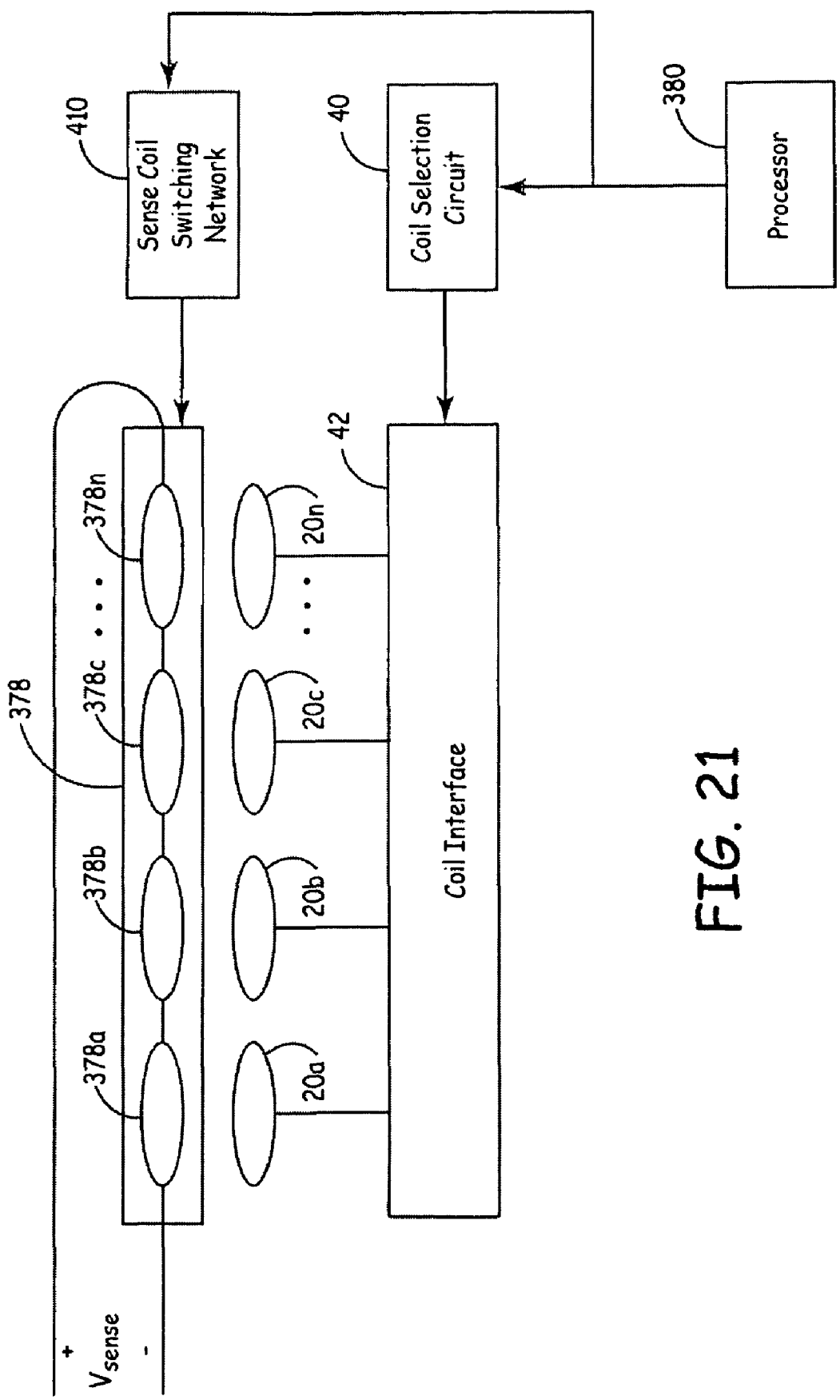
FIG. 21 is an embodiment of multiple clamping coils utilized in a field-limiting circuit in conjunction with an array of primary coils.

FIG. 20 is a block diagram of one embodiment of a field limiting circuit 58. A processor 380 is provided that may be the same, or a different processor than, a processor that is included in control circuit 61 of FIG. 11A, and may be the same, or a different processor than, processor 68 of FIG. 14. Processor 380 programmably provides a selected digital value to a digital-to-analog converter (DAC) 382 that selects the clamp voltage, $V_{clamp}$. DAC 382 supplies this analog voltage level to a positive input of differential amplifier 384. The negative input of this differential amplifier is connected through a resistor 386 and a diode 388 to sense coil 378 (shown in cross-section in FIG. 20). In one embodiment, field limiting circuit 58 may instead be coupled to multiple sense coils, as shown in FIG. 21 and discussed below.

During a recharge session, flux through sense coil 378 increases as recharge coupling improves between primary coil 374 (not shown in FIG. 20) and secondary coil 370. This results in an increase in the maximum voltage amplitude $V_{max\_sense}$ across the sense coil 378. As this occurs, and before the voltage at the input of the diode reaches an amplitude at which amplifier 384 is sinking current, current primarily flows through resistors R1 386 and R2 390. When the voltage at node 393 increases beyond the clamping voltage $V_{clamp}$, amplifier 384 begins to limit the voltage at the output of diode 388 so that the voltage can no longer increase. Voltage at the positive terminal of the diode 388 (and hence across sense coil 378) will thereby also be limited according to the following equation:

$$V_{max\_sense} = V_{clamp}(1 + R1/R2) + V_{diode}$$

In this equation, $V_{diode}$ is the voltage drop across diode 388 when that component is forward biased at the point when the voltage at node 393 is approximately equal to $V_{clamp}$. R1 and R2 are the resistance values selected for resistors 386 and 388, respectively.

At the time limiting of voltage across sense coil 378 begins, current begins to flow through amplifier in the direction of arrow 392. This removes energy from the system, limits voltage across primary coil 370, and thereby limits the amount of magnetic flux that the couples the primary coil to the sense coil 378 according to the following:

$$B_{max\_sense} = V_{sense}/(N_{sense} A_{sense} 2\pi f)$$

According to another aspect, a programmable switch 394 that is controllable by processor 380 may be used to couple node 396 to the input of one or more rechargeable batteries 398 such that the current generated during the voltage clamping operation is used to recharge one or more rechargeable batteries 398. Rechargeable batteries 398 may be one or more of the batteries included in power source 35 (FIG. 11A), and which is used to power external power source 34, making external power source 34 more suitable for ambulatory form factors. Batteries 398 may be further coupled to a battery charger 399 that is adapted to be plugged into a standard outlet for use in supplementing the charge received via the voltage clamping operation.

Recharging of the batteries 398 in the foregoing manner is possible when $V_{clamp}$ is selected such that $V_{max\_sense}$ is greater than the battery voltage $V_{batt}$ plus the voltage drop across the diode 388, $V_{diode}$. When $V_{clamp}$ is selected such that $V_{max\_sense}$ is less than battery voltage $V_{batt}$ plus the voltage drop across the diode 388, switch 394 should be programmed in the other position to allow current that is being sunk by the amplifier 384 according to arrow 392 to be dissipated by resistor 400.

The system of FIG. 20 further includes circuit 402, which includes two diodes that are used to tune the frequency at which modulation circuit 38 drives the primary coil 20. In particular, the diodes of circuit 402 will provide a waveform that will indicate the resonant frequency of the system. This waveform is provided via interconnection 403 to modulation circuit 38, which for the current discussion is assumed to be a self-tuning modulation circuit of the type known in the art. When node 405 of field limiting circuit 58 is connected to share a common ground with modulation circuit 38, modulation circuit 38 is able to utilize the signal on interconnection 403 to determine the optimal frequency at which to drive primary coil 20. In particular, modulation circuit 38 will become tuned to drive the system and primary coil 374 at the resonant frequency of the system. This will maximize the efficiency of the coupling between the primary and secondary coils.

It may be noted that the maximum battery voltage will vary over the life of the battery, which may affect the position in which switch 394 should be placed. To address this, battery characteristic data 84 may be stored within storage device(s) 60 for use in making a determination as to whether field limiting circuit 58 should be utilized to recharge batteries 398 based on a selected clamping voltage, $V_{clamp}$. For instance, battery characteristic data may reflect that for a given type of battery, battery voltage will decrease as the number of times the battery has undergone recharge increases. Thus, for a given clamping voltage, field limiting circuit 58 may be used to recharge batteries 398 during the latter life of the batteries but not during later battery life when the battery voltage is higher. Of course, when a battery replacement operation occurs, it will generally be necessary to synchronize battery characteristic data 84 so that battery life, and hence battery voltage, may be accurately determined.

In one embodiment, a compare circuit 407 may be provided to compare the programmable value $V_{clamp}$ to $V_{sense}$. At the point when sense coil 378 begins to draw energy out of the system by causing current to flow through amplifier in the direction of arrow 392, compare circuit 407 provides a signal on interface 408 to modulation circuit 38. This occurs when $V_{sense}$ reaches $V_{max\_sense}$. As previously described, $$V_{max\_sense} = V_{clamp}(1+R1/R2)+V_{diode}$$

When $V_{sense}$ has reached $V_{max\_sense}$ as indicated by the signal on interface 408, it may be desirable for modulation circuit 38 to reduce the voltage and/or current at which the primary coil is being driven, since at least some of the energy currently being supplied to the primary coil 20 so that not as much energy is being drained from the system by field limiting circuit 58. This will conserve the amount of energy used to drive primary coil 20, which is particularly desirable in a system wherein power source 35 includes batteries.

$V_{sense}$ and $B_{max\_sense}$ can be determined empirically, and may be selected to correspond to the maximum magnetic field strength value to be experienced by a patient. For instance, external power source 34 may be used to expose the patient to a predetermined magnetic field strength value, as set by government regulations, and as measured by a magnetic field sensor positioned on the patient's skin. When the patient is experiencing this maximum allowable magnetic field strength, the maximum magnetic field strength at the sense coil $B_{max\_sense}$ may be measured. Similarly, the corresponding voltage across the coil at this time, $V_{sense}$, may be measured and used to determine the clamping voltage $V_{clamp}$. This data may be stored as translation data 82. Many such data sets may be stored in this manner for use in regulating the maximum magnetic field value to which a patient is exposed.

In the foregoing manner, the magnetic field strength at a sense coil 378 may be limited by controlling voltage across the sense coil. According to one embodiment, sense coil 378 may comprise multiple sense coils. This is necessary when there are multiple primary coils 20, as follows.

FIG. 21 is a block diagram of an embodiment wherein sense coil 378 is a coil array comprises multiple coils 378a-378n. In this embodiment, multiple primary coils 20a-20n are coupled to a coil selection circuit 40 in the manner shown in FIG. 11A. Processor 380 may, in one embodiment, utilize coil selection circuit 40 to select which of the primary coils 20a-20n will be activated to perform recharge based on various feedback signals, as discussed above.

Each of the primary coils 20a-20n is associated with a respective one of sense coils 378a-378n. A sense coil switching network 410 is provided interconnect each sense coil that corresponds to an activated primary coil (that is, a primary coil that is inductively coupled to a secondary coil of an IMD) in an in-series configuration. As an example, FIG. 21 illustrates a scenario wherein all primary coils 20a-20n are activated, and therefore all corresponding sense coils are switched in-series with one another by sense coil switching network 410. In an embodiment wherein all primary coils but coil 20b are activated, sense coils 378a and 378c-378n will be switched into an in-series configuration with one another, and coil 378b will be omitted from this coil configuration, and so on.

The total voltage drop across all of the selected in-series sense coils is $V_{sense}$ when modulation circuit 38 drives all of the activated primary coils 20 in phase with one another. In this manner, the total flux through all activated in-series sense coils (and thus, through all activated primary coils) may be limited by field limiting circuit 58 of FIG. 20. This allows the total maximum magnetic field strength to which a patient is exposed using a multiple-coil configuration to be limited programmably to a level associated with one or more regulations 72 and/or one or more device limitations 80 based on a patient device profile 78. The type of multiple-coil configurations that may be used in this embodiment include, but are not limited to, those embodiments shown in the drawings, including those of FIGS. 5-10.

It may be noted that the foregoing description discusses use of the various aspects of the invention with long-range recharge systems and/or in systems wherein recharge may be passively initiated. However, many aspects of the current invention are applicable to any type of recharge system. For instance, the use of patient preferences, regulations, patient device profiles, and device limitations may be employed with any type of recharge. Similarly, automatically-acquired location, regulatory, and other patient data may be beneficially utilized in regard to any type of recharge system. The types of feedback systems and methods shown in FIG. 11A-FIG. 18 may be employed with any type of recharge configuration, including short- and long-range recharge configurations. Similarly, the various embodiments described for limiting magnetic field strength may be practiced with any type of recharge system and method. Thus, the embodiments described herein, and the applications described for use of the embodiments, are to be considered exemplary only and not limiting, and the present invention is limited only by the claims that follow.

What is claimed is:

1. A charging system for an implantable medical device (IMD) having a secondary coil, comprising:
   a primary coil;
   a storage device storing information describing a regulatory requirement;
   a sensor sensing a condition during operation of the charging system indicating whether the regulatory requirement is being met; and
   a modulation circuit operatively coupled to the primary coil, the sensor, and the storage device, wherein the modulation circuit is adapted to drive the primary coil in a manner determined by the regulatory requirement and the sensed condition when the primary coil is in proximity to the secondary coil.

2. The charging system of claim 1 wherein the sensor is a temperature sensor and the condition is a temperature in excess of the regulatory requirement.

3. The charging system of claim 1 wherein a second medical device is in proximity to the IMD, the regulatory requirement describes a requirement associated with the second medical device, and the condition indicates whether the requirement associated with the second medical device is being met.

4. The charging system of claim 1 wherein the storage device further stores patient preference data and the condition further indicates whether the patient preference has been met.

5. The charging system of claim 1, further including a control circuit to automatically acquire the regulatory requirement based on location information.

6. The charging system of claim 5, further including a location detector to automatically acquire the location information.

7. The charging system of claim 1, wherein the condition is a maximum magnetic field strength, and further including a field limiting circuit coupled to the modulation circuit to limit the maximum magnetic field strength at the primary coil.

8. The charging system of claim 7, further including at least one rechargeable battery, and wherein the field limiting circuit recharges the rechargeable battery while limiting the maximum magnetic field strength.

9. The charging system of claim 7, further comprising a sense coil in proximity to the primary coil and wherein the field limiting circuit controls the maximum magnetic field strength by limiting voltage across the sense coil.

10. The charging system of claim 7, further including multiple primary coils, each coupled to the modulation circuit, wherein the field limiting circuit limits total magnetic flux through all of the primary coils.

11. A system, comprising:
an implantable medical device having a secondary coil;
a primary coil to inductively couple to the secondary coil;
a storage device to store information describing a regulatory requirement indicative of magnetic field strength; and
a circuit coupled to the primary coil and to the storage device, wherein the circuit is adapted to control a manner in which the primary coil is energized based on a determination of whether the regulatory requirement is being met.

12. The system of claim 11, further including at least one sensor to make the determination of whether the regulatory requirement is being met.

13. The system of claim 11, further including a second implantable medical device in proximity to receive energy from the primary coil, and wherein the regulatory requirement governs limitations associated with the energy received by the second implantable medical device from the primary coil.

14. The system of claim 11, wherein the circuit includes a field limiting circuit to control maximum magnetic field strength at the primary coil.

15. The system of claim 14, wherein the primary coil is energized by a rechargeable power source and the field limiting circuit charges the rechargeable power source.

16. The system of claim 14, further including multiple primary coils to be inductively coupled to the secondary coil, and wherein the field limiting circuit selectably limits an amount of magnetic flux coupling multiple ones of the primary coils.

17. The system of claim 11, further including a control circuit to automatically initiate retrieval of the information describing the regulatory requirement.

18. The system of claim 11, wherein the circuit coupled to the primary coil controls the manner in which the primary coil is energized based on one or more of a group selected from patient preferences, device limitations describing limitations of at least one other medical device, and a patient profile describing a patient in which the implantable medical device is implanted.

19. The system of claim 11, wherein the circuit includes a modulation circuit to modulate a signal driving the primary coil by controlling at least one of a group consisting of signal amplitude, signal frequency, and signal duty cycle.

20. A method for use with an implantable medical device, comprising:
storing in a programmable storage device data that describes a regulatory requirement controlling energizing a secondary coil of the implantable medical device;
using a primary coil to energize the secondary coil;
sensing a condition associated with energizing the secondary coil; and
modifying a manner of energizing the primary coil based on whether the regulatory requirement is met as determined by the sensed condition.

21. The method of claim 20, further including:
determining a location of use of the implantable medical device; and
automatically selecting the regulatory requirement based on the location.

22. The method of claim 20, wherein the regulatory requirement describes a requirement that is associated with a medical device other than the implantable medical device, and further including translating the regulatory requirement into data describing the condition associated with energizing the secondary coil.

23. The method of claim 20, wherein modifying the manner of energizing the primary coil is further based on at least one of patient preferences, a patient device profile, and device limitations.

24. The method of claim 20, wherein modifying the manner of energizing the primary coil includes limiting a strength of a magnetic field at the primary coil.

25. The method of claim 24, wherein limiting the strength of the magnetic field at the primary coil recharges a battery that is employed to energize the primary coil.

26. A system, comprising:
a primary coil to recharge a power source of an implantable medical device (IMD) implanted in a patient, the IMD being in proximity to one or more additional medical devices carried by the patient;
a storage device to store information describing a regulatory requirement limiting a condition experienced by at least one of the additional medical devices during the recharge session; and
a circuit coupled to the primary coil and to the storage device, wherein the circuit is adapted to control a manner in which the primary coil is energized based on a determination of whether the regulatory requirement is being met.

27. The system of claim 26, wherein the regulatory requirement further limits a condition experienced by the IMD during the recharge session.

28. The system of claim 26, wherein the condition is a maximum magnetic field strength to which the at least one of the additional medical devices is exposed.

29. The system of claim 26, wherein the circuit includes a sense coil to inductively couple to the primary coil to limit the maximum magnetic field strength to which the at least one of the additional medical devices is exposed when the primary coil is recharging the power source.

30. The system of claim 26, further including:

multiple primary coils used to recharge the power source;

multiple sense coils, each to inductively couple to a respective one of the multiple primary coils; and wherein the circuit limits the maximum magnetic field strength to which the at least one of the additional medical devices is exposed by limiting a cumulative amount of magnetic flux coupling all of the multiple sense coils.

31. A charging system for an implantable medical device (IMD) having a secondary coil, comprising:

a primary coil;

a storage device adapted to store information describing a regulatory requirement and further to store patient preference data associated with a patient preference;

a sensor adapted to sense a condition during operation of the charging system indicating whether the regulatory requirement is being met and further indicating whether the patient preference has been satisfied; and a modulation circuit operatively coupled to the primary coil, the sensor, and the storage device, wherein the modulation circuit is adapted to drive the primary coil in a manner determined by the regulatory requirement, the patient preference and the sensed condition when the primary coil is in proximity to the secondary coil.

32. The charging system of claim 31 wherein the condition is a temperature.

33. A method for use with an implantable medical device, comprising:

storing in a programmable storage device data that describes a regulatory requirement controlling energizing a secondary coil of the implantable medical device and data indicative of a patient preference;

using a primary coil to energize the secondary coil;

sensing a condition associated with energizing the secondary coil; and modifying a manner of energizing the primary coil based on whether the regulatory requirement is met and whether the patient preference is being satisfied as determined by the sensed condition.

34. The method of claim 33, wherein the sensed condition is a temperature.

35. A system, comprising:

an implantable medical device having a secondary coil;

a primary coil to inductively couple to the secondary coil;

a storage device adapted to store information describing a regulatory requirement and data indicative of a patient preference; and a circuit coupled to the primary coil and to the storage device, wherein the circuit is adapted to control a manner in which the primary coil is energized based on a determination of whether the regulatory requirement is being met and whether the patient preference is being satisfied.

* * * * *